(12) United States Patent
Soll et al.

(10) Patent No.: US 9,133,209 B2
(45) Date of Patent: Sep. 15, 2015

(54) INSECTICIDAL 4-AMINO-THIENO[2,3-D]-PYRIMIDINE COMPOUNDS AND METHODS OF THEIR USE

(75) Inventors: Mark David Soll, Alpharetta, GA (US); Charles Meng, Johns Creek, GA (US); Matthias Pohlman, Freinsheim (DE); Ernst Baumann, Dudenhofen (DE); Ralph Paulini, Bad Duerkheim (DE)

(73) Assignee: MERIAL, INC., Duluth, GA (US)

( * ) Notice: Subject to any disclaimer, the term of this patent is extended or adjusted under 35 U.S.C. 154(b) by 521 days.

(21) Appl. No.: 13/386,194

(22) PCT Filed: Jul. 29, 2010

(86) PCT No.: PCT/US2010/043717
§ 371 (c)(1),
(2), (4) Date: May 17, 2012

(87) PCT Pub. No.: WO2011/014660
PCT Pub. Date: Feb. 3, 2011

(65) Prior Publication Data
US 2012/0252667 A1    Oct. 4, 2012

Related U.S. Application Data

(60) Provisional application No. 61/229,769, filed on Jul. 30, 2009.

(51) Int. Cl.
*C07D 495/04* (2006.01)
*A01N 43/90* (2006.01)
*A01N 47/02* (2006.01)

(52) U.S. Cl.
CPC ............. *C07D 495/04* (2013.01); *A01N 43/90* (2013.01); *A01N 47/02* (2013.01)

(58) Field of Classification Search
CPC ............................ C07D 495/04; A01N 43/90
USPC .................................. 544/278; 504/100, 241
See application file for complete search history.

(56) References Cited

U.S. PATENT DOCUMENTS

2006/0089370 A1* 4/2006 Brewster et al. .............. 544/278

FOREIGN PATENT DOCUMENTS

EP             424125    * 4/1991 .................... 544/278

* cited by examiner

*Primary Examiner* — Susanna Moore
(74) *Attorney, Agent, or Firm* — Judy Jarecki-Black; Peter Dolan; Merial, Inc.

(57) ABSTRACT

The compounds of general formula I, wherein X, $R^1$, $R^2$, $R^3$ and A are defined as in the description, are of the class of 4-amino-thieno[2,3-d]-pyrimidine compounds useful to control pests that damage plants and crops, and parasites that harm animals:

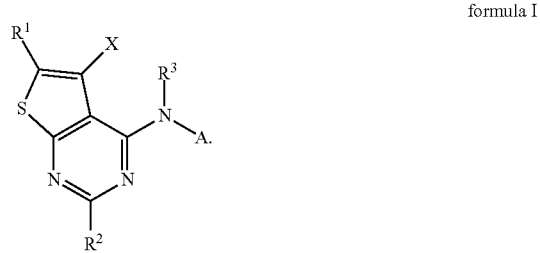

formula I

20 Claims, No Drawings

INSECTICIDAL 4-AMINO-THIENO[2,3-D]-PYRIMIDINE COMPOUNDS AND METHODS OF THEIR USE

CROSS REFERENCE TO RELATED APPLICATIONS

This application claims the benefit of priority to U.S. Provisional Patent Application No. 61/229,769 filed Jul. 30, 2009, which is incorporated herein in its entirety by reference.

FIELD OF THE INVENTION

The present invention relates to new pesticidal and parasiticidal 4-amino-thieno[2,3-d]-pyrimidine compounds, compositions comprising the compounds, and new methods of their use.

BACKGROUND OF THE INVENTION

Animal pests destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating animal pests. In particular, animal pests such as insects and acaridae are difficult to be effectively controlled.

Thienopyrimidines are known and have been described in prior art. 4-Amino-thienopyrimidines have been mentioned in EP-A 0370704 and U.S. Pat. No. 5,141,941 as aralkylamine derivatives having bactericidal properties, and in EP 424125 further aralkylamine derivatives are described for their fungicidal use. 4-Amino-thienopyrimidine derivative compositions have also been described in DE-A 2654090 and U.S. Pat. No. 4,146,716 for controlling fungal, viral and bacterial plant disease and insect damage. In EP-A 0452002 N-substituted-thienopyrimidin-4-amines having fungicidal, insecticidal and miticidal utility are disclosed. JP-A 2004-238380 describes the preparation of 4-phenylethylaminopyrimidine and their uses as pesticides. Thieno-pyrimidine compounds having fungicidal activity have been described in WO 2006/047397 and US 2006/0089370 A1 and WO2007/046809. Alkoxylated 4-amino-thieno[2,3-d]-pyrimidine compounds have been described WO 2007/135029 and US 2009/0203524 A1. N-substituted 4-amino-thieno[2,3-d]-pyrimidine compounds with herbicidal, growth-regulating and insecticidal activities have been described in EP-A 0447891. Each of the publications cited above are incorporated herein by reference in their entirety.

Any published applications and patents cited herein, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

Although some thienopyrimidines with insecticidal activity have been reported, there continues to be a need for compounds with improved pesticidal and parasiticidal activity, in particular against acaridae.

It is therefore an object of the present invention to provide methods and compounds having a good pesticidal activity, especially against difficult to control insects and acaridae.

SUMMARY

It has been found that the objects of the invention are solved by new 4-amino-thieno[2,3-d]-pyrimidine derivatives of the general formula I:

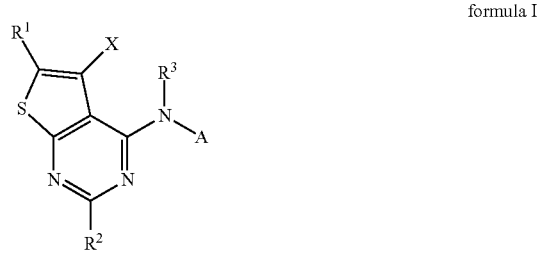

formula I wherein variables X, A, $R^1$, $R^2$ and $R^3$ are as described below, or pharmaceutically acceptable salts thereof.

In one embodiment, the invention provides agricultural and veterinary compositions comprising an effective amount of at least one compound of the formula I, or an enantiomer, diastereomer or salt thereof, in combination with an agriculturally acceptable or veterinarily acceptable carrier.

In another embodiment, the invention provides agricultural or veterinary compositions comprising at least one compound of formula I in combination with another pesticidal or parasiticidal active agent and an agriculturally acceptable or veterinarily acceptable carrier.

In another embodiment, the invention provides methods and uses for combating or controlling animal pests, for protecting crops or for protecting plant propagation material with compounds of formula I or compositions comprising the compounds, comprising contacting the crop, the plant propagation material or the animal pests, their habit, breeding ground, food supply, plant, seed, soil, area, material or environment in which the animal pests are growing or may grow, or the materials, plants, seeds, soils, surfaces or spaces to be protected from animal pest attack or infestation with a pesticidally effective amount of at least one compound of the formula I, or an enantiomer, diastereomer or salt thereof.

Also provided are methods and uses for combating parasites in or on animals, for treating, controlling or preventing parasitic infections or infestations on animals, comprising administering a parasiticidally effective among of at least one compound of formula I or a composition comprising the compound, or an enantiomer, diastereomer or veterinarily acceptable salt thereof, to the animal.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are apparent from and encompassed by, the following Detailed Description.

DETAILED DESCRIPTION

The present invention provides new and inventive 4-amino-thieno[2,3-d]pyrimidine derivatives of the general formula I:

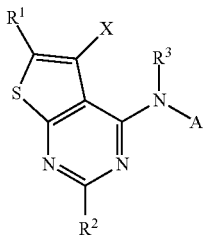

formula I wherein

X is selected from halogen, $C_1$-$C_{10}$-alkyl or $C_1$-$C_{10}$-haloalkyl;

$R^1$ is selected from the group consisting of hydrogen, halogen, formyl, $C_1$-$C_{10}$-alkyl, $C_1$-$C_{10}$-alkenyl, $C_1$-$C_{10}$ alkynyl, $C_1$-$C_{10}$-haloalkyl, $C_1$-$C_{10}$-haloalkenyl, $C_1$-$C_{10}$-haloalkynyl, $C_1$-$C_{10}$-alkoxy, $C_1$-$C_6$-alkoxy-$C_1$-$C_6$-alkyl, $C_1$-$C_{10}$-haloalkoxy, $C_1$-$C_{10}$-alkylthio, $C_1$-$C_{10}$-haloalkylthio, $C_1$-$C_{10}$-alkylsulfinyl, $C_1$-$C_{10}$-haloalkylsulfinyl, $C_1$-$C_{10}$-alkylsulfonyl, $C_1$-$C_{10}$-haloalkyl-sulfonyl, $C_1$-$C_{10}$-alkylamino, $C_1$-$C_{10}$-haloalkylamino, di($C_1$-$C_{10}$-alkyl)amino, di($C_1$-$C_{10}$)-haloalkylamino, CN, —$CR^3$=NOH, —$CR^3$=$NOCH_3$ and —$CR^3$=$NOC_2H_5$;

$R^2$ is selected from the group consisting of hydrogen, halogen, $C_1$-$C_{10}$-alkyl, $C_1$-$C_{10}$-haloalkyl, $C_1$-$C_{10}$-alkoxy, $C_1$-$C_6$-alkoxy-$C_1$-$C_6$-alkyl, $C_1$-$C_{10}$-haloalkoxy, $C_1$-$C_{10}$-alkylthio, $C_1$-$C_{10}$-haloalkylthio, $C_1$-$C_{10}$-alkylsulfinyl, $C_1$-$C_{10}$-haloalkylsulfinyl, $C_1$-$C_{10}$-alkylsulfonyl, $C_1$-$C_{10}$-haloalkyl-sulfonyl, $C_1$-$C_{10}$-alkylamino, $C_1$-$C_{10}$-haloalkylamino, di($C_1$-$C_{10}$-alkyl)amino and di($C_1$-$C_{10}$)-haloalkylamino;

$R^3$ is selected from hydrogen, $C_1$-$C_{10}$-alkyl or $C_1$-$C_{10}$-haloalkyl;

A is

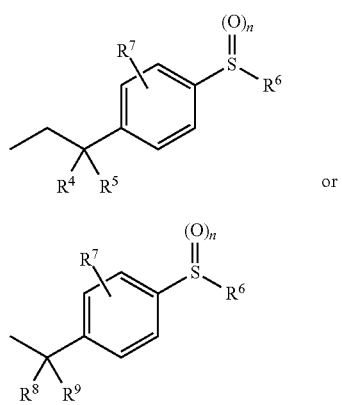

wherein n is 0, 1 or 2;

$R^4$, $R^5$, $R^8$ and $R^9$ are selected independently from one another from hydrogen, CN, $C_1$-$C_{10}$-alkyl or $C_1$-$C_{10}$-haloalkyl;

$R^6$ is selected from the group consisting of $C_1$-$C_{10}$ fluorohaloalkyl, $C_2$-$C_{10}$ fluorohaloalkenyl, $C_2$-$C_{10}$ fluorohaloalkynyl and $C_3$-$C_7$ fluorohalocycloalkyl, wherein the carbon atoms of the aforementioned fluorohaloalkyl radicals may further be substituted with $C_1$-$C_{10}$-alkoxy, $C_1$-$C_{10}$-haloalkoxy, cyano and (C=O)$R^q$, and wherein $R^q$ is selected from the group consisting of amino, $C_1$-$C_6$-alkoxy, $C_1$-$C_6$-haloalkoxy, $C_1$-$C_6$-alkylamino, $C_1$-$C_6$-haloalkylamino, di($C_1$-$C_6$-alkyl)amino and di($C_1$-$C_6$)-haloalkylamino;

$R^7$ is selected from the group consisting of hydrogen, halogen, CN, $C_1$-$C_{10}$-alkyl, $C_1$-$C_{10}$-haloalkyl, $C_1$-$C_{10}$-alkoxy, $C_1$-$C_6$-alkoxy-$C_1$-$C_6$-alkyl, $C_1$-$C_{10}$-haloalkoxy, $C_1$-$C_{10}$-alkylthio and $C_1$-$C_{10}$-haloalkylthio;

and/or at least an enantiomer, diastereomer or agriculturally or veterinary acceptable salt thereof.

Depending on the substitution pattern, the compounds of the present invention can contain one or more chiral centers, in which case they are present as enantiomer or diastereomer mixtures. Subject matter of this invention is not only compositions containing these mixtures but also those containing the pure enantiomers or diastereomers.

The compounds of present invention may also be present in different crystalline modifications for the inventive use, and may also differ in their biological activity. These different crystalline modifications are also subject of the present invention.

In addition, the compounds of the invention may exist as hydrates or solvates, in which a certain stoichiometric amount of water or a solvent is associated with the molecule in the crystalline form. The hydrates and solvates of the compounds of formula I are also the subject of the invention.

The present invention relates to insecticidal and parasiticidal methods applying such compounds and including the following embodiments:

agricultural and veterinary compositions comprising an amount of at least one compound of the formula I, or an enantiomer, diastereomer or salt thereof;

the use of a compound of formula I, or an enantiomer, diastereomer or salt thereof for combating or controlling animal pests;

a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal pest attack or infestation with a pesticidally effective amount of at least one compound of the formula I, or an enantiomer, diastereomer or salt thereof;

a method for protecting crops from attack or infestation by animal pests, which comprises contacting a crop with a pesticidally effective amount of at least one compound of the formula I, or an enantiomer, diastereomer or salt thereof;

a method for the protection of plant propagation material, especially seeds, from soil insects and of the seedlings' roots and shoots from soil and foliar insects comprising contacting the plant propagation material, especially the seeds, before sowing and/or after pregermination with at least one compound of the formula I, or the enantiomers, diastereomers or salts thereof;

seeds comprising a compound of the formula I, or an enantiomer, diastereomer or salt thereof;

the use of compounds of formula I, or the enantiomers, diastereomers or veterinary acceptable salts thereof for combating parasites in and on animals;

the use of compounds of formula I, or the enantiomers, diastereomers or veterinary acceptable salts thereof, in the manufacture of a medicament for combating parasites in and on animals;

a method for treating, controlling, preventing or protecting animals against infestation or infection by parasites which comprises orally, topically or parenterally administering or applying to the animals a parasiticidally effective amount of a compound of formula I, or the enantiomers, diastereomers and/or veterinary acceptable salt thereof;

a process for the preparation of a composition for treating, controlling, preventing or protecting animals against infestation or infection by parasites which comprises a parasiticidally effective amount of an compound of formula I, or the enantiomers, diastereomers and/or veterinary acceptable salt thereof.

Compared to those compounds disclosed in WO 2006/047397 comprising un-substituted thioalkylsubstitutents, the fluorohalogenated thioalkylsubstituted 4-amino-thieno[2,3-d]-pyrimidine compounds of the present invention show surprisingly a better insecticidal activity. They also show a better efficacy than alkoxylated 4-amino-thieno[2,3-d]-pyrimidine compounds of WO 2007/135029.

The compounds of the formula I, and their agriculturally or veterinary acceptable salts are highly active against animal pest, i.e. harmful arthropodes and nematodes, especially against difficult to control insects and acaridae.

Moreover, salts of the compounds of the formula I are preferably agriculturally or veterinary acceptable salts. They can be formed in a customary method, e.g. by reacting the compound with an acid of the anion in question if the compound of formula I has a basic functionality or by reacting an acidic compound of formula I with a suitable base.

Useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy) ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of formula I with an acid of the corresponding anion, preferably of hydrochloric acid, hydrobromic acid, sulfuric acid, phosphoric acid or nitric acid.

Terms used herein will have their customary meaning in the art unless specified. In the definition of formula I shown above, the substituents have the following meanings:

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine. In one embodiment of the invention, the halogen is fluorine or chlorine.

The term "$C_1$-$C_{10}$-alkyl" as used herein and the alkyl moieties of alkylamino and dialkylamino refer to a saturated straight-chain or branched hydrocarbon group including those having 1 to 10 carbon atoms, 1 to 6 carbon atoms and 1 to 4 carbon groups, respectively. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_1$-$C_{10}$-haloalkyl" as used herein refers to a straight-chain or branched saturated alkyl group having 1 to 10 carbon atoms (as mentioned above), where some or all of the hydrogen atoms in these groups may be replaced by halogen atoms as mentioned above. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "$C_1$-$C_2$-fluoroalkyl" as used herein refers to a $C_1$-$C_2$-alkyl which carries 1, 2, 3, 4 or 5 fluorine atoms, for example difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "$C_1$-$C_{10}$-fluorohaloalkyl" as used herein refers to a straight-chain or branched saturated alkyl group having 1 to 10 carbon atoms (as mentioned above) which carries at least one fluorine atoms, and where some or all of the remaining hydrogen atoms in these groups may be replaced by halogen atoms selected independently from one another from fluorine, bromine, chlorine or iodine.

The term, "$C_1$-$C_{10}$-alkoxy" as used herein refers to a straight-chain or branched saturated alkyl group having 1 to 10 carbon atoms (as mentioned above) which is attached via an oxygen atom. Examples include $C_1$-$C_6$-alkoxy such as methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "$C_1$-$C_{10}$-haloalkoxy" as used herein refers to a $C_1$-$C_{10}$-alkoxy group as mentioned above which is partially or fully substituted by fluorine, chlorine, bromine and/or iodine, i.e., for example, $C_1$-$C_6$-haloalkoxy such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy. In one embodiment of the invention, "$C_1$-$C_{10}$-haloalkoxy" is selected from the group consisting of chloromethoxy, fluoromethoxy, difluoromethoxy, trifluoromethoxy, 2-fluoroethoxy, 2-chloroethoxy and 2,2,2-trifluoroethoxy.

The term "$C_1$-$C_6$-alkoxy-$C_1$-$C_6$-alkyl" as used herein refers to $C_1$-$C_6$-alkyl which is substituted by $C_1$-$C_6$-alkoxy as mentioned above, i.e., for example, $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl and the like.

The term "$C_1$-$C_6$-alkoxy-$C_1$-$C_6$-alkoxy" as used herein refers to $C_1$-$C_6$-alkoxy which is substituted by $C_1$-$C_6$-alkoxy as mentioned above, i.e., for example, $OCH_2$—$OCH_3$, $OCH_2$—$OC_2H_5$, n-propoxymethoxy, $OCH_2$—$OCH(CH_3)_2$, n-butoxymethoxy, (1-methylpropoxy)methoxy, (2-methylpropoxy)methoxy, $OCH_2$—$OC(CH_3)_3$, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(n-propoxy)propoxy, 2-(1-methylethoxy)propoxy, 2-(n-butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(n-propoxy)propoxy, 3-(1-methylethoxy)propy, 3-(n-butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(n-propoxy)butoxy, 2-(1-methylethoxy)butoxy, 2-(n-butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(n-propoxy)butoxy, 3-(1-methylethoxy)butoxy, 3-(n-butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(n-propoxy)butoxy, 4-(1-methylethoxy)butoxy, 4-(n-butoxy)butoxy, 4-(1-methylpropoxy)butoxy, 4-(2-methylpropoxy)butoxy, 4-(1,1-dimethylethoxy)butoxy and the like.

The term "$C_1$-$C_4$-alkoxy-$C_1$-$C_4$-alkoxy-$C_1$-$C_4$-alkoxy" as used herein refers to $C_1$-$C_4$-alkoxy which is substituted by $C_1$-$C_4$-alkoxy-$C_1$-$C_4$-alkoxy as mentioned above, i.e., for example, 2-(2-methoxyethyloxy)ethyloxy, 2-(2-ethoxyethyloxy)ethyloxy.

The term "$C_1$-$C_{10}$-alkylcarbonyl" as used herein refers to a straight-chain or branched saturated alkyl group having 1 to 10 carbon atoms (as mentioned above) bonded via the carbon atom of the carbonyl group at any bond in the alkyl group. Examples include $C_1$-$C_6$-alkylcarbonyl such as $CO$—$CH_3$, $CO$—$C_2H_5$, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl and the like.

The term "$C_1$-$C_{10}$-alkoxycarbonyl" as used herein refers to a straight-chain or branched alkoxy group (as mentioned above) having 1 to 10 carbon atoms attached via the carbon atom of the carbonyl group. Examples include ($C_1$-$C_6$-alkoxy)carbonyl, for example $CO$—$OCH_3$, $CO$—$OC_2H_5$, $COO$—$CH_2$—$C_2H_5$, $CO$—$OCH(CH_3)_2$, n-butoxycarbonyl, $CO$—$OCH(CH_3)$—$C_2H_5$, $CO$—$OCH_2$—$CH(CH_3)_2$, $CO$—$OC(CH_3)_3$, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl.

The term "$C_1$-$C_{10}$-alkylthio ($C_1$-$C_{10}$-alkylsulfanyl:$C_1$-$C_{10}$-alkyl-S—)" as used herein refers to a straight-chain or branched saturated alkyl group having 1 to 10 carbon atoms (as mentioned above) which is attached via a sulfur atom, for example $C_1$-$C_4$-alkylthio such as methylthio, ethylthio, propylthio, 1-methylethylthio, butylthio, 1-methylpropylthio, 2-methylpropylthio or 1,1-dimethylethylthio.

The term "$C_1$-$C_{10}$-alkylsulfinyl" ($C_1$-$C_{10}$-alkyl-S(=O)—), as used herein refers to a straight-chain or branched saturated hydrocarbon group (as mentioned above) having 1 to 10 carbon atoms bonded through the sulfur atom of the sulfinyl group at any bond in the alkyl group. Examples include $C_1$-$C_6$-alkylsulfinyl: SO—$CH_3$, SO—$C_2H_5$, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

The term "$C_1$-$C_{10}$-alkylsulfonyl" ($C_1$-$C_{10}$-alkyl-S(=O)$_2$—) as used herein refers to a straight-chain or branched saturated alkyl group having 1 to 10 carbon atoms (as mentioned above) which is bonded via the sulfur atom of the sulfonyl group at any bond in the alkyl group. Examples include $C_1$-$C_6$-alkylsulfonyl such as $SO_2$—$CH_3$, $SO_2$—$C_2H_5$, n-propylsulfonyl, $SO_2$—CH($CH_3$)$_2$, n-butylsulfonyl, 1-methylpropylsulfonyl, 2-methylpropylsulfonyl, $SO_2$—C($CH_3$)$_3$, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl and the like.

The term "$C_2$-$C_{10}$-alkenyl" as used herein refers to a straight-chain or branched unsaturated hydrocarbon group having 2 to 10 carbon atoms and at least one double bond in any position. "$C_2$-$C_{10}$-alkenyl" groups may include more than one double bond in the chain. Examples include, but are not limited to, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "$C_2$-$C_{10}$-fluorohaloalkenyl" or "$C_2$-$C_{10}$-fluorohaloalkynyl" as used herein refers to a straight-chain or branched unsaturated alkenyl or alkynyl group having 2 to 10 carbon atoms and containing at least one double, respectively one triple bond (as mentioned above), which carries at least one fluorine atoms, and where some or all of the remaining hydrogen atoms in these groups may be replaced by halogen atoms selected independently from one another from fluorine, bromine, chlorine or iodine.

The term "$C_3$-$C_{10}$-cycloalkyl" as used herein refers to a monocyclic hydrocarbon radical having 3 to 10 carbon atoms, in particular 3 to 8 carbon atoms, e.g. cyclopropyl, cyclobutyl, cyclopentyl, cyclohexyl, cycloheptyl, cyclooctyl, cyclononyl or cyclodecyl.

The term "$C_3$-$C_{10}$-fluorohalocycloalkyl" as used herein refers to a monocyclic hydrocarbon radical having 3 to 10 carbon atoms, which carries at least one fluorine atoms, and where some or all of the remaining hydrogen atoms in these groups may be replaced by halogen atoms selected independently from one another from fluorine, bromine, chlorine or iodine.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine.

With respect to the different methods of use according to the invention, particular preference is given to the following meanings of the substituents and variables of the 4-amino-thieno[2,3-d]-pyrimidine compounds of formula I, in each case on their own or in combination:

Preferred are 4-amino-thieno[2,3-d]-pyrimidine compounds of formula I, wherein A is A2 and $R^9$ is selected from the group consisting of hydrogen, $C_1$-$C_{10}$-alkyl or $C_1$-$C_{10}$-haloalkyl.

More preferred are 4-amino-thieno[2,3-d]-pyrimidine compounds of formula I, wherein A is A2, $R^8$ is hydrogen and $R^9$ is $C_1$-$C_{10}$-alkyl or $C_1$-$C_{10}$-haloalkyl.

Especially preferred are those 4-amino-thieno[2,3-d]-pyrimidine compounds of formula I, wherein A is A2, $R^8$ is hydrogen and $R^9$ is $C_1$-$C_{10}$-alkyl or $C_1$-$C_{10}$-haloalkyl, and wherein the substituents at the chiral carbon atom, where $R^8$ and $R^9$ are bound to, are in (S)-configuration.

Most preferred are 4-amino-thieno[2,3-d]-pyrimidine compounds of formula I, wherein A is A2, $R^8$ is hydrogen and $R^9$ is methyl.

Especially preferred are those 4-amino-thieno[2,3-d]-pyrimidine compounds of formula I, wherein A is A2, $R^8$ is hydrogen and $R^9$ is methyl and wherein the substituents at the chiral carbon atom, where $R^8$ and $R^9$ are bound to, are in (S)-configuration.

Preferred are 4-amino-thieno[2,3-d]-pyrimidine compounds of formula I, wherein $R^7$ is hydrogen.

Preferred are 4-amino-thieno[2,3-d]-pyrimidine compounds of formula I, wherein $R^6$ is $C_1$-$C_{10}$-fluorohaloalkyl.

More preferred are 4-amino-thieno[2,3-d]-pyrimidine compounds of formula I, wherein $R^6$ is trifluoromethyl.

Preferred are 4-amino-thieno[2,3-d]-pyrimidine compounds of formula I, wherein $R^3$ is hydrogen.

Preferred are 4-amino-thieno[2,3-d]-pyrimidine compounds of formula I, wherein $R^2$ is selected from the group consisting of hydrogen, halogen, $C_1$-$C_{10}$-alkyl and $C_1$-$C_{10}$-haloalkyl.

More preferred are 4-amino-thieno[2,3-d]-pyrimidine compounds of formula I, wherein $R^2$ is hydrogen.

Preferred are 4-amino-thieno[2,3-d]-pyrimidine compounds of formula I, wherein $R^1$ is selected from the group consisting of hydrogen, halogen, $C_1$-$C_{10}$-alkyl and $C_1$-$C_{10}$-haloalkyl.

More preferred are 4-amino-thieno[2,3-d]-pyrimidine compounds of formula I, wherein $R^1$ is hydrogen or chloro.

Preferred are 4-amino-thieno[2,3-d]-pyrimidine compounds of formula I, wherein X is halogen.

More preferred are 4-amino-thieno[2,3-d]-pyrimidine compounds of formula I, wherein X is chloro.

Preferred are 4-amino-thieno[2,3-d]-pyrimidine compounds of formula I, wherein n is 0.

Especially preferred are 4-amino-thieno[2,3-d]-pyrimidine compounds of the general formula I-S:

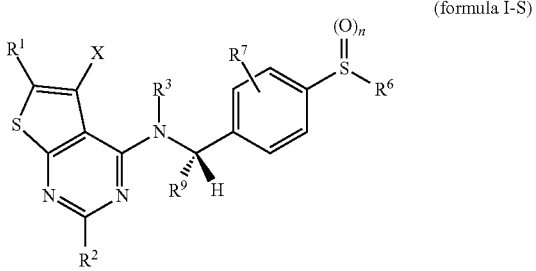

(formula I-S)

wherein n, X, $R^1$, $R^2$, $R^3$, $R^6$, $R^7$ and $R^9$ are defined as for formula I.

More preferred are 4-amino-thieno[2,3-d]-pyrimidine compounds of the general formula I-S, wherein X, $R^1$, $R^2$, $R^3$, $R^6$, $R^7$ and $R^9$ represent the preferred substituents as defined above for formula I, alone or in combination.

Mostly preferred are 4-amino-thieno[2,3-d]-pyrimidine compounds of the general formula I-S, wherein n is 0 or 1, X is chloro, $R^1$ is hydrogen or halogen, $R^2$, $R^3$ and $R^7$ are hydrogen, $R^6$ is $C_1$-$C_{10}$-fluorohaloalkyl and $R^9$ is $C_1$-$C_{10}$-alkyl or $C_1$-$C_{10}$-haloalkyl.

Preparation Methods 4-amino-thieno[2,3-d]pyrimidine compounds of formula I according to the present invention can be prepared as described in WO 2007/135029, which refers to EP 0447 891 B, wherein the 4-amino-thieno[2,3-d]pyrimidine compounds are prepared starting from thiophene compounds (II).

A thiophene derivative of formula (II)

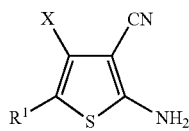

(II)

wherein X and $R^1$ is defined as above, is reacted with a dialkyl amide (III)

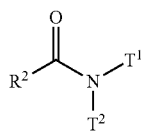

(III)

wherein $T^1$ and $T^2$ are independently from one another $C_1$-$C_4$-alkyl or form together with the nitrogen a 5 to 7-membered saturated heterocycle and $R^2$ is defined as above, in presence of an excess of a phosphoryl halogenide as e.g. 2 to 20 mol of phosphoryl chloride or phosphoryl bromide compared to 1 mol of (II) in order to provide a thieno-(2,3-d)-pyrimidine derivative of formula (Ia)

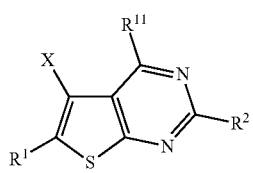

(Ia)

wherein $R^{11}$ is chloro or bromo.

Compounds of formula (Ia) obtained as described above can be converted by substitution of the halogen atom in position 4 by another nucleophilic rest according to known methods as described in 'The Chemistry of Heterocyclic compounds', "The pyrimidines", ed. D. J. Brown, J. Wiley & Sony, New York, London, Vol. 16, (1962); Vol. 16, Suppl. 1, Vol. 16, Suppl. 2 (1985).)

They are converted to the corresponding compounds of formula I by the substitution of $R^{11}$ by $NR^3A$ as described in EP-A 447 891.

Examples of suitable dialkyl-amides (III) are N,N-dimethylformamide, N,N-dimethyl-acetamide, N,N-diethylformamide, N,N-diethylacetamide, N,N-dimethylpropionamide and N,N-dimethyl benzoic acid amide.

As mentioned above, the reaction has to be conducted in presence of an excess of phosphoryl chloride or phosphoryl bromide compared to the thiophene derivative (II). Advantageously the reaction may take place with the phosphoryl halogenide as a solvent. Preferably 2 to 6 mol of phosphoryl halogenide are used per mol of the thiophene derivative (II).

In general the molar ratio of the thiophene derivative (II) to the N,N-dialkyl amide (III) is from 1:1 to 1:5.

The reaction is usually conducted in an inert solvent, such as chlorobenzole, nitrobenzole, benzoic acid methyl ester, methylene chloride, dichlorobenzol, trichlorobenzole, benzoic acid ethyl ester, chloroform, tetrachlorocarbon, one of the N,N-dialkyl amides listed above, trichloroethane, hexamethylphosphoric triamide (HMPT) or tetrachloroethylene. Preferred solvent are phosphoryl chloride and phosphoryl bromide or one of the N,N-dialkyl amides listed above.

The reaction has a sufficient reaction speed above 20° C. At temperatures above 150° C. the reaction specificity drops. Preferably the reaction is conducted in a temperature range of 50 to 110° C.

By the use of catalytic amounts of a Lewis acid as potassium chloride, sodium chloride, iron (III) chloride, aluminum chloride, zinc chloride, tin chloride, antimony pentafluoride, boron trifluoride or titanium tetrachloride or of a basic catalyst as N,N-dimethyl aniline or N,N-diethyl aniline an increase of yield and an enhancement of reaction speed can be achieved.

Another process of preparation of 4-amino-thieno[2,3-d] pyrimidine compounds of formula I is provided by reacting according to common practice compounds of formula (IV)

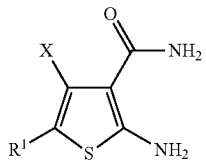

(IV)

wherein X and $R^1$ is defined as above, with an acid anhydride, that contains at least a residue $R^2$—CO—, or a carbonic acid $R^2$—COOH, or an adduct of a carbonic acid and a Lewis acid, wherein $R^2$ has the respective meaning as described above, to compounds of formula (Ib):

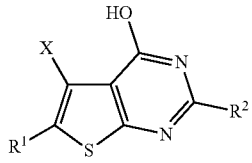

(Ib)

Compounds of formula (Ib) are converted with a phosphoryl halogenide to compounds of formula (Ia) as defined above. It is suitable in certain cases to conduct this conversion in two steps, thereby isolating the intermediate compounds of formula (VI):

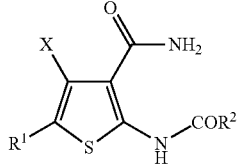

(VI)

In general the acid anhydride or the adduct is used in amounts from 100 to 500 mol-%, preferably from 100 to 300 mol-%, in regard of compounds (VI).

The carbonic acid anhydrides containing at least one residue $R^2$—CO—, can be provided out of two carbonic acids $R^2$—COOH, as pivalic acid, propionic acid or acetic acid; or out of one carbonic acid $R^2$—COOH and one oxo acid, as phosphoric acid or sulfuric acid.

Preferred carbonic acids $R^2$—COOH are those with 1 to 4 carbon atoms, especially formic acid and acetic acid.

Further, adducts of a carbonic acid $R^2$—COOH and a Lewis acid, as zinc chloride, boron trifluoride and titanium tetrachloride are also suitable.

The conversion from (IV) to (Ib) is advantageously conducted in an inert solvent, such as N,N-dialkyl amides, preferably N,N-dimethyl formamide and N,N-dimethyl acetamide, N-methyl-pyrrolidone, N,N-dimethyl propylene urea or hexamethylphosphoric triamide at temperatures from (−10) to 150° C., preferably from 20 to 120° C., more preferably from 80 to 120° C.

In order to isolate intermediate compounds (VI), the reaction temperature should be chosen from (−10) to 80° C.

In general a base such as triethylamine, N-methyl-pyrrolidone or N,N-dimethylaniline should be added in an excess of 1 to 10-times, preferably in an excess of 1 to 5-times, compared to the carbonic acid anhydride, the carbonic acid or the carbonic-acid-Lewis-acid-adduct.

The addition of a water removing agent, such as dicyclohexyl carbodiimide, or a Vilsmeier reagent can speed up the reaction and increase the yield of compounds of formula (Ib).

The hydroxy group in position 4 of compound of formula (Ib) can be substituted by chloro or bromo according to common practice, e.g. with phosphoryl chloride or phosphoryl bromide.

Finally chloro and bromo in position 4 is substituted by $NR^3A$ as described e.g. in EP-A 447 891.

The thio-substituted aryl group A of $NR^3A$ can be prepared by alkylation of the respective thiophenols with fluoroalkyl compounds, which bear suitable leaving groups like e.g. halogen atoms.

Furthermore, according to Scheme 1 by conversion of thiophene compounds of formula (II) with orthoesters (V), wherein $R^{12}$ is a $C_1$-$C_4$-alkyl, to derivatives of formula (VI), and subsequent cyclization in presence of an amine $NR^3A$, thieno[2,3-d]pyrimidine compounds of formula (I) according to the present invention can be obtained.

Scheme 1:

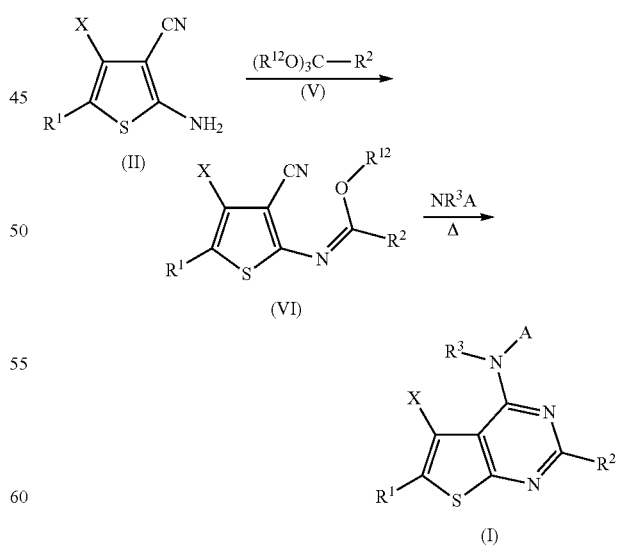

The latest described reaction scheme is known from DE-A 26 54 090. The thiophene derivative (II) and (IV) can be obtained according to the instructions disclosed in EP-A1 0193 885.

In principle, enantiomerically enriched, substituted benzyl amines NR³A can be obtained either by resolution of the corresponding racemate or via asymmetric synthesis from achiral precursors.

Synthesis 2008, 14, 2283-2287 describes a typical procedure where Lipases are used as catalysts for chiral resolution of racemic, substituted benzylamines. According to the following scheme 2 the racemates would be reacted e.g. with esters of aliphatic carboxylic esters of small alkyls or alkenyl (wherein $R^{13}$ is e.g. $C_1$-$C_4$-alkyl, $C_1$-$C_4$-alkenyl and $R^{14}$ is e.g. an optionally substituted $C_1$-$C_4$-alkyl like $CH_2OCH_3$) and after completion of the reaction, one enantiomer would be converted to the corresponding amide whereas the 2$^{nd}$ enantiomer would remain unreacted.

Scheme 2:

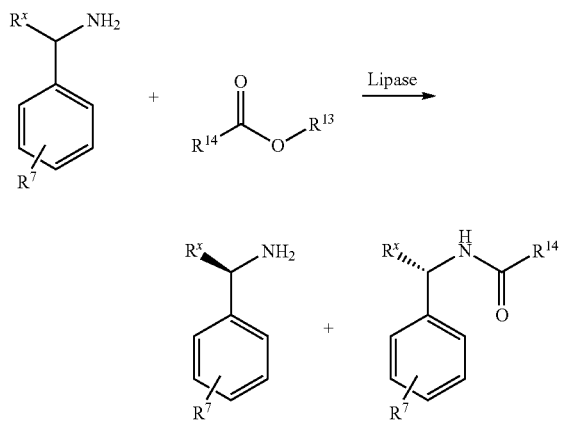

wherein $R^x$ is defined as for $R^4$, $R^5$, $R^7$ or $R^8$ as above.

In cases where $R^x$ is a small alkyl group such as methyl, typically the (S)-enantiomer would be acylated whereas the (R)-enantiomer would remain unreacted. Upon separation of the reaction mixture eg via distillation or chromatography the (R)-enantiomer would be used directly and the (S)-enantiomer could be obtained after cleavage of the amide bond after hydrolysis according to the following scheme 3:

Scheme 3:

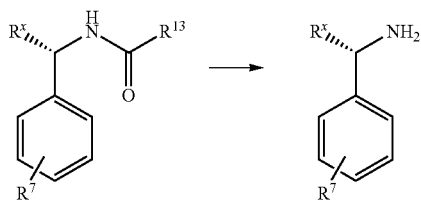

Different synthetic procedures that lead to enantiomerically enriched or enantiopure substituted benzylamines via asymmetric synthesis are described in literature. Typically, they involve the reduction of a C=N bond as described in scheme 4. Appropriate substrates for this type of reduction are oxime ethers (e.g. $R^{15}$=$C_1$-$C_4$-alkoxy) as described eg in Org. Lett. 2007, 9, 1793-1795 or chiral sulfoximines (e.g $R^{15}$=S(=O) tBu) as described eg in *J. Org. Chem.* 2006, 71, 6859-6862.

Scheme 4:

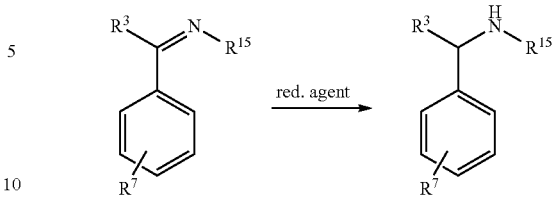

In order to obtain salts, which are suitable for agricutural or veterinary use, the 4-amino-thieno[2,3-d]pyrimidine compounds of formula I can be reacted with conventional salt builders as hydrochloric acid, hydrobromic acid, hydroiodic acid, sulfuric acid, phosphoric acid, formic acid, acetic acid, oxalic acid, benzene sulfonic acid, p-toluol-sulfonic acid, dodecylbenzene sulfonic acid, methyl bromide, dimethyl sulfate or diethyl sulfate in temperature range of 0 to 150° C., preferably 20 to 120° C.

The formation of the salt is usually conducted in a dissolving or diluting agent. Suitable are e.g. aliphatic hydrocarbons as n-pentane, n-hexane or petrol ether, aromatic hydrocarbons, as benzole, toluole or xylole, benzyne or ethers as diethyl ether, methyl-tert.-butyl ether, tetrahydrofuran or dioxane, further ketones, as acetone, methyl-ethyl-ketone or methyl-isopropyl-ketone, as well as halogenated hydrocarbons as chlorobenzole, methylene chloride, ethylene chloride, chloroform or tetrachloro ethylene. Also mixtures of those solvents can be used.

For the preparation of salts of compounds of formula I the educts are employed usually in a stoichiometric ratio. The excess of one or the other component can be useful.

In the preparation methods described, the variables X, $R^1$, $R^2$, and $R^3$ have the meanings as defined above, in particular the meanings mentioned as being preferred.

If individual compounds cannot be prepared via the above-described routes, they can be prepared by derivitization of other compounds I or by customary modifications of the synthesis routes described.

The reaction mixtures are worked up in the customary manner, for example by mixing with water, separating the phases, and, if appropriate, purifying the crude products by chromatography, for example on alumina or silica gel. Some of the intermediates and end products may be obtained in the form of colorless or pale brown viscous oils, which are freed or purified from volatile components under reduced pressure and at moderately elevated temperature. If the intermediates and end products are obtained as solids, they may be purified by recrystallization or digestion.

Pests

The compounds of the formula I and their salts are in particular suitable for efficiently controlling arthropodal pests such as arachnids, myriapedes and insects as well as nematodes.

Animal pests controlled by the compounds of formula I include for example:

Insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia* subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabs, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis;

beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctate, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza forum, Oscinella frit, Pegomya hysocyami, Phorbia antiqua, Phorbia brassicae, Phorbia coarctate, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;* thrips (Thysanoptera), e.g. *Dichromothrips corbetti, Dichromothrips* ssp., *Frankliniella fusca, Frankliniella occidentalis, Frankliniella tritici, Scirtothrips citri, Thrips oryzae, Thrips palmi* and *Thrips tabaci,* termites (Isoptera), e.g. *Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis,* and *Coptotermes formosanus;* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis;* bugs, aphids, leafhoppers, whiteflies, scale insects, cicadas (Hemiptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schnideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribisnigri, Nilaparvata lugens, Pemphigus bursarius, Perkinsiella saccharicida, Phorodon humuli, Psylla mali, Psylla pini, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma* spp., and *Arilus critatus;* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp., *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile;* crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus varie-* gatus, *Hieroglyphus daganensis, Kraussaria angulifera, Calliptamus italicus, Chortoicetes terminifera,* and *Locustana pardalina;* arachnoidea, such as arachnids (Acarina), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis;* Araneida, e.g. *Latrodectus mactans,* and *Loxosceles reclusa;* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* centipedes (Chilopoda), e.g. *Scutigera coleoptrata,* millipedes (Diplopoda), e.g. *Narceus* spp.,

Earwigs (Dermaptera), e.g. *forficula auricularia,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

Collembola (springtails), e.g. *Onychiurus* ssp.

They are also suitable for controlling Nematodes: plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of the formula I and their salts are also useful for controlling arachnids (Arachnoidea), such as acarians (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis.*

Compounds of the formula I are particularly useful for controlling insects, preferably sucking or piercing insects such as insects from the genera Thysanoptera, Diptera and Hemiptera, in particular the following species: *Thysanoptera: Frankliniella fusca, Frankliniella occidentalis, Frankliniella tritici, Scirtothrips citri, Thrips oryzae, Thrips palmi* and *Thrips tabaci,*

Diptera, e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctate, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctate, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;*

Hemiptera, in particular aphids: *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryp-* tomyzus ribis, *Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla pini, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Tnialeunodes vaponanionum, Toxoptera aurantiiand,* and *Viteus vitifolii;*

Compounds of the formula I are particularly useful for controlling insects of the orders Hemiptera and Thysanoptera.

Formulations

For use in a method according to the present invention, the compounds of formula I can be converted into the customary formulations, e.g. solutions, emulsions, suspensions, dusts, powders, pastes, granules and directly sprayable solutions. The use form depends on the particular purpose and application method. Formulations and application methods are chosen to ensure in each case a fine and uniform distribution of the compound of the formula I according to the present invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Solvents/carriers, which are suitable, are e.g.:
solvents such as water, aromatic solvents (for example Solvesso products, xylene and the like), paraffins (for example mineral fractions), alcohols (for example methanol, butanol, pentanol, benzyl alcohol), ketones (for example cyclohexanone, gamma-butyrolactone), pyrrolidones (N-metyhl-pyrrolidone (NMP), N-octylpyrrolidone NOP), acetates (glycol diacetate), alkyl lactates, lactones such as g-butyrolactone, glycols, fatty acid dimethylamides, fatty acids and fatty acid esters, triglycerides, oils of vegetable or animal origin and modified oils such as alkylated plant oils. In principle, solvent mixtures may also be used.
carriers such as ground natural minerals and ground synthetic minerals, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants include alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, and sorbitol esters.

Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives include, for example, dichlorophen and benzyl alcohol hemiformal.

Suitable thickeners include compounds which confer a pseudoplastic flow behavior to the formulation, i.e. high viscosity at rest and low viscosity in the agitated stage. Mention may be made, in this context, for example, of commercial thickeners based on polysaccharides, such as Xanthan Gum® (Kelzan® from Kelco), Rhodopol® 23 (Rhone Poulenc) or Veegum® (from R.T. Vanderbilt), or organic phyllosilicates, such as Attaclay® (from Engelhardt). Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof. Biocides can be added to stabilize the compositions according to the invention against attack by microorganisms. Suitable biocides are, for example, based on isothiazolones such as the compounds marketed under the trademarks Proxel® from Avecia (or Arch) or Acticide® RS from Thor Chemie and Kathon® MK from Rohm & Haas. Suitable antifreeze agents are organic polyols, for example ethylene glycol, propylene glycol or glycerol. These are usually employed in amounts of not more than 10% by weight, based on the total weight of the active compound composition. If appropriate, the active compound compositions according to the invention may comprise 1 to 5% by weight of buffer, based on the total amount of the formulation prepared, to regulate the pH, the amount and type of the buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

Substances which are suitable for the preparation of directly sprayable solutions, emulsions, pastes or oil dispersions include mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compound of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

The following are non-limiting examples of formulations:

1. Products for dilution with water. For seed treatment purposes, such products may be applied to the seed diluted or undiluted.

A) Water-Soluble Concentrates (SL, LS)

10 parts by weight of the active compound is dissolved in 90 parts by weight of water or a water-soluble solvent. As an alternative, wetters or other auxiliaries are added. The active compound dissolves upon dilution with water, whereby a formulation with 10% (w/w) of active compound is obtained.

B) Dispersible Concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.

C) Emulsifiable Concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.

D) Emulsions (EW, EO, ES)

25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.

E) Suspensions (SC, OD, FS)

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.

F) Water-Dispersible Granules and Water-Soluble Granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-Dispersible Powders and Water-Soluble Powders (WP, SP, SS, WS)

75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable Powders (DP, DS)

5 parts by weight of the active compound are ground finely and mixed intimately with 95 parts by weight of finely divided kaolin. This gives a dustable product having 5% (w/w) of active compound.

J) Granules (GR, FG, GG, MG)

0.5 part by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV Solutions (UL)

10 parts by weight of the active compound is dissolved in 90 parts by weight of an organic solvent, for example xylene. This gives a product having 10% (w/w) of active compound, which is applied undiluted for foliar use.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

Mixtures

In the method of this invention compounds of formual I may be applied with other active ingredients, for example with other pesticides, insecticides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

The following list M of pesticides together with which the compounds according to the invention can be used and with which potential synergistic effects might be produced, is intended to illustrate the possible combinations, but not to impose any limitation:

M.1. Organo(thio)phosphate compounds: acephate, azamethiphos, azinphosethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamate compounds: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroid compounds: acrinathrin, allethrin, d-cis-trans allethrin, d-trans allethrin, bifenthrin, bioallethrin, bioallethrin S-cylclopentenyl, bioresmethrin, cyclopothrin, cyfluthrin, beta-cyfluthrin, cyhalothrin, lambda-cyhalothrin, gammacyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonsits: amitraz;

M.21. Ryanodine receptor modulators: flubendiamide and the phtalamid compound (R)-, (S)-3-Chlor-N-1-{2-methyl-4-[1,2,2,2-tetrafluor-1-(trifluormethyl)ethyl]phenyl}-N2-(1-methyl-2-methylsulfonylethyl)phthalamid (M21.1)

M.22. Isoxazoline compounds: 4-[5-(3,5-Dichloro-phenyl)-5-trifluoromethyl-4,5-dihydro-isoxazol-3-yl]-2-methyl-N-pyridin-2-ylmethyl-benzamide (M22.1), 4-[5-(3,5-Dichloro-phenyl)-5-trifluoromethyl-4,5-dihydro-isoxazol-3-yl]-2-methyl-N-(2,2,2-trifluoro-ethyl)-benzamide (M22.2), 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide (M22.3), 4-[5-(3,5-Dichloro-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.4) and 4-[5-(3,5-Dichlorophenyl)-5-trifluoromethyl-4,5-dihydro-isoxazol-3-yl]-N-[(methoxyimino)methyl]-2-methylbenzamide (M22.5);

M.23. Anthranilamide compounds: chloranthraniliprole, cyantraniliprole,

5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M23.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M23.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M23.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M23.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M23.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M23.6), N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester (M23.7), N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M23.8), N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M23.9), N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M23.10), N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M23.11) and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M23.12);

M.24. Malononitrile compounds: 2-(2,2,3,3,4,4,5,5-octafluoropentyl)-2-(3,3,3-trifluoro-propyl)malononitrile ($CF_2H-CF_2-CF_2-CF_2-CH_2-C(CN)_2-CH_2-CH_2-CF_3$) (M24.1) and 2-(2,2,3,3,4,4,5,5-octafluoropentyl)-2-(3,3,4,4,4-pentafluorobutyl)-malonodinitrile ($CF_2H-CF_2-CF_2-CF_2-CH_2-C(CN)_2-CH_2-CH_2-CF_2-CF_3$) (M24.2);

M.25. Microbial disruptors: *Bacillus thuringiensis* subsp. *Israelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

M.26. Aminofuranone compounds:

4-{[(6-Bromopyrid-3-yl)methyl](2-fluoroethyl)amino}furan-2(5H)-on (M26.1),

4-{[(6-Fluoropyrid-3-yl)methyl](2,2-difluoroethyl)amino}furan-2(5H)-on (M26.2),

4-{[(2-Chloro-1,3-thiazolo-5-yl)methyl](2-fluoroethyl)amino}furan-2(5H)-on (M26.3), 4-{[(6-Chloropyrid-3-yl)methyl](2-fluoroethyl)amino}furan-2(5H)-on (M26.4), 4-{[(6-Chloropyrid-3-yl)methyl](2,2-difluoroethyl)amino}furan-2(5H)-on (M26.5), 4-{[(6-Chloro-5-fluoropyrid-3-yl)methyl](methyl)amino}furan-2(5H)-on (M26.6), 4-{[(5,6-Dichloropyrid-3-yl)methyl](2-fluoroethyl)amino}furan-2(5H)-on (M26.7), 4-{[(6-Chloro-5-fluoropyrid-3-yl)methyl](cyclopropyl)amino}furan-2(5H)-on (M26.8), 4-{[(6-Chloropyrid-3-yl)methyl](cyclopropyl)amino}furan-2(5H)-on (M26.9) and 4-{[(6-Chloropyrid-3-yl)methyl](methyl)amino}furan-2(5H)-on (M26.10);

M.27. Various compounds: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, N—R'-2,2-dihalo-1-R"cyclopropanecarboxamide-2-(2,6-dichloro-$\alpha,\alpha,\alpha$-trifluoro-p-tolyl)hydrazone or N—R'-2,2-di(R''')propionamide-2-(2,6-dichloro-$\alpha$,$\alpha,\alpha$-trifluoro-p-tolyl)-hydrazone, wherein R' is methyl or ethyl, halo is chloro or bromo, R" is hydrogen or methyl and R''' is methyl or ethyl, 4-But-2-ynyloxy-6-(3,5-dimethyl-piperidin-1-yl)-2-fluoro-pyrimidine (M27.1), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester (M27.2) and 8-(2-Cyclopropylmethoxy-4-trifluoromethyl-phenoxy)-3-(6-trifluoromethyl-pyridazin-3-yl)-3-aza-bicyclo[3.2.1]octane (M27.3).

The commercially available compounds of the group M may be found in The Pesticide Manual, 13th Edition, British Crop Protection Council (2003) among other publications.

Lepimectin is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Metaflumizone and its preparation have been described in EP-A1 462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. AKD 1022 and its preparation have been described in U.S. Pat. No. 6,300,348. Chloranthraniliprole has been described in WO 01/70671, WO 03/015519 and WO 05/118552. Cyantraniliprole has been described in WO 01/70671, WO 04/067528 and WO 05/118552. The anthranilamides M23.1 to M23.6 have been described in WO 2008/72743 and WO 200872783, those M23.7 to M23.12 in WO2007/043677. The phthalamide M 21.1 is known from WO 2007/101540. Cyflumetofen and its preparation have been described in WO 04/080180. The aminoquinazolinone compound pyrifluquinazon has been described in EP A 109 7932. Sulfoximine sulfoxaflor has been described in WO 2006/060029 and WO 2007/149134. The alkynylether compound M27.1 is described e.g. in JP 2006131529. Organic sulfur compounds have been described in WO 2007060839. The isoxazoline compounds M 22.1 to M 22.5 have been described in e.g. WO2005/085216, WO 2007/079162 and WO 2007/026965. The aminofuranone compounds M 26.1 to M 26.10 have been described eg. in WO 2007/115644. The pyripyropene derivative M 27.2 has been described in WO 2008/66153 and WO 2008/108491. The pyridazin compound M 27.3 has been described in JP 2008/115155. Malononitrile compounds as those (M24.1) and (M24.2) have been described in WO 02/089579, WO 02/090320, WO 02/090321, WO 04/006677, WO 05/068423, WO 05/068432 and WO 05/063694.

Fungicidal mixing partners are those selected from the group consisting of acylalanines such as benalaxyl, metalaxyl, ofurace, oxadixyl, amine derivatives such as aldimorph, dodine, dodemorph, fenpropimorph, fenpropidin, guazatine, iminoctadine, spiroxamin, tridemorph, anilinopyrimidines such as pyrimethanil, mepanipyrim or cyrodinyl, antibiotics such as cycloheximid, griseofulvin, kasugamycin, natamycin, polyoxin or streptomycin, azoles such as bitertanol, bromoconazole, cyproconazole, difenoconazole, dinicona-zole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol, dicarboximides such as iprodion, myclozolin, procymidon, vinclozolin, dithiocarbamates such as ferbam, nabam, maneb, mancozeb, metam, metiram, propineb, polycarbamate, thiram, ziram, zineb, heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine, copper fungicides such as Bordeaux mixture, copper acetate, copper oxychloride, ba-sic copper sulfate, nitrophenyl derivatives such as binapacryl, dinocap, dinobuton, nitrophthalisopropyl, phenylpyrroles such as fenpiclonil or fludioxonil, sulfur, other fungicides such as acibenzolar-S-methyl, benthiavalicarb, carpropamid, chlorothalonil, cyflufenamid, cymoxanil, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid, strobilurins such as azoxystrobin, dimoxystrobin, fluoxastrobin, kresoximmethyl, me-tominostrobin, orysastrobin, picoxystrobin or trifloxystrobin, sulfenic acid derivatives such as captafol, captan, dichlofluanid, folpet, tolylfluanid, cinnemamides and analogs such as dimethomorph, flumetover or flumorph.

Applications

Due to their excellent activity, the compounds of formulae I may be used for controlling animal pests. Accordingly, the present invention also provides a method for controlling animal pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula I or a salt thereof or a composition as defined above.

Preferably, the method of the invention serves for protecting plant propagation material (such as seed) and the plant which grows therefrom from animal pest attack or infestation and comprises treating the plant propagation material (such as seed) with a pesticidally effective amount of a compound of the formula I or an agriculturally acceptable salt thereof as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

In the sense of the present invention, "animal pests" are preferably selected from arthropods and nematodes, more preferably from harmful insects, arachnids and nematodes, and even more preferably from insects, acarids and nematodes.

The invention further provides an agricultural composition for combating such animal pests, which comprises such an amount of at least one compound of formula I or at least one agriculturally useful salt thereof and at least one inert liquid and/or solid agronomically acceptable carrier that has a pesticidal action and, if desired, at least one surfactant.

Such a composition may contain a single active compound of formula I or a salt thereof or a mixture of several active compounds of formulae I or their salts according to the present invention. The composition according to the present invention may comprise an individual isomer or mixtures of isomers as well as individual tautomers or mixtures of tautomers.

The animal pest, i.e. the insects, arachnids and nematodes, the plant, soil or water in which the plant is growing can be contacted with the present compounds of formula I or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of formula I or the pesticidal compositions comprising them may be used to protect growing plants and crops from attack or infestation by animal pests, especially insects, acaridae or arachnids by contacting the plant/crop with a pesticidally effective amount of compounds of formula I. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

The compounds of the present invention are employed as such or in form of compositions by treating the insects or the plants, plant propagation materials, such as seeds, soil, surfaces, materials or rooms to be protected from insecticidal attack with an insecticidally effective amount of the active compounds. The application can be carried out both before and after the infection of the plants, plant propagation materials, such as seeds, soil, surfaces, materials or rooms by the insects.

The present invention also includes a method of combating animal pests which comprises contacting the animal pests, their habitat, breeding ground, food supply, cultivated plants, seed, soil, area, material or environment in which the animal pests are growing or may grow, or the materials, plants, seeds, soils, surfaces or spaces to be protected from animal attack or infestation with a pesticidally effective amount of a mixture of at least one active compound of formula I.

Moreover, animal pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

The compounds of the invention can also be applied preventively to places at which occurrence of the pests is expected.

The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8., Protein Eng Des Sel. 2004 January; 17(1):57-66, Nat. Protoc. 2007; 2(5):1225-35., Curr Opin Chem. Biol. 2006 October; 10(5): 487-91. Epub 2006 Aug. 28., Biomaterials. 2001 March; 22(5):405-17, Bioconjug Chem. 2005 January-February; 16(1):113-21).

The term "cultivated plants" is to be understood also including plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering.

Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus Bacillus, particularly from Bacillus thuringiensis, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example Photorhabdus spp. or Xenorhabdus spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are disclosed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (Diptera), and butterflies and moths (Lepidoptera) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against Phytophthora infestans derived from the mexican wild potato Solanum bulbocastanum) or T4-lysozym (e.g. potato cultivars capable of synthesizing these proteins with increased resistance against bacteria such as Erwinia amylvora). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for ex-ample oil crops that produce health-promoting long-chain omega-3 fatty acids or unsaturated omega-9 fatty acids (e.g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e.g. Amflora® potato).

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of formula I are effective through both contact (via soil, glass, wall, bed net, carpet, plant parts or animal parts), and ingestion (bait, or plant part).

The compounds of the invention may also be applied against non-crop insect pests, such as ants, termites, wasps, flies, mosquitos, crickets, or cockroaches. For use against said non-crop pests, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickiness, moisture retention or aging characteristics.

The bait employed in the composition is a product, which is sufficiently attractive to incite insects such as ants, termites, wasps, flies, mosquitos, crickets etc. or cockroaches to eat it.

The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active compound.

Formulations of compounds of formula I as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of formula I and their respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethyl-cyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic dienes, such as butadiene.

The impregnation of curtains and bednets is done in general by dipping the textile material into emulsions or dispersions of the insecticide or spraying them onto the nets.

The compounds of formula I and their compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

Seed Treatment

The compounds of formula I are also suitable for the treatment of seeds in order to protect the seed from insect pest, in particular from soil-living insect pests and the resulting plant's roots and shoots against soil pests and foliar insects.

The compounds of formula I are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the general formula I or a salt thereof. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of formula I for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®)

In the treatment of seed, the application rates of the compounds I are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising a compound of the formula I, or an agriculturally useful salt of I, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

Animal Health Applications

The compounds of formula I or the enantiomers or veterinarily acceptable salts thereof are in particular also effective for combating parasites in and on animals.

An object of the present invention is therefore also to provide new methods to control parasites in and on animals. Another object of the invention is to provide safer pesticides for animals. Another object of the invention is further to provide pesticides with improved potency for animals that may be used in lower doses than existing pesticides. And another object of the invention is to provide pesticides for animals, which provide a long residual control of the parasites.

The invention also relates to compositions containing a parasiticidally effective amount of compounds of formula I or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of one or more compounds of formula I, or the enantiomers or veterinarily acceptable salts thereof, or a composition comprising the compounds.

The present invention also provides a non-therapeutic method for treating, controlling, preventing and protecting animals against infestation and infection by parasites, which comprises applying to a locus a parasiticidally effective amount of a compound of formula I or the enantiomers or veterinarily acceptable salts thereof or a composition comprising it.

In another embodiment, the invention provides compositions comprising a parasiticidally effective amount of one or more compounds of formula I, or enantiomers, or veterinarily acceptable salts thereof, in combination with one or more other active agents and an acceptable carrier, for combating parasites in and on animals. Methods for treating, controlling, preventing and protecting animals against infestation and infection by parasites comprising administering an effective amount of one or more compounds of formula I in combination with other active agents are also provided.

The invention also provides a process for the preparation of a composition for treating, controlling, preventing or protecting animals against infestation or infection by parasites which comprises including a parasiticidally effective amount of a compound of formula I or the enantiomers or veterinarily acceptable salts thereof in a composition comprising it.

The invention relates further to the use of compounds of formula I for treating, controlling, preventing or protecting animals against infestation or infection by parasites.

The invention relates also to the use of a compound of formula I, or a composition comprising it, for the manufacture of a medicament for the therapeutic treatment of animals against infections or infestations by parasites.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling. Furthermore, it will be apparent to one of skill in the art that the adsorption, distribution, metabolism and elimination of the compounds of the invention, when used to combat parasites in and on animals, is not predictable based on the effectiveness of the compounds in agricultural applications.

Surprisingly it has now been found that compounds of formula I are effective for combating endo- and ectoparasites in and on animals.

Compounds of formula I or the enantiomers or veterinarily acceptable salts thereof and compositions comprising them are preferably used for controlling and preventing infestations and infections animals including warm-blooded animals (including humans), birds and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or the enantiomers or veterinarily acceptable salts thereof and compositions comprising them are preferably used for controlling and preventing infestations and infections animals including warm-blooded animals (excluding humans), birds and fish. They are for example suitable for controlling and preventing infestations and infections in mammals excluding humans.

Compounds of formula I or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I or the enantiomers or veterinarily acceptable salts thereof and compositions comprising them are effective for systemic and/or non-systemic control of ecto- and/or endoparasites. They are active against all or some stages of development.

The compounds of formula I are especially useful for combating ectoparasites. In various embodiments for treatment against ectoparasites, the ectoparasite is one or more insect or arachnid including those of the genera *Ctenocephalides, Rhipicephalus, Dermacentor, Ixodes, Boophilus, Ambylomma, Haemaphysalis, Hyalomma, Sarcoptes, Psoroptes, Otodectes, Chorioptes, Hypoderma, Damalinia, Linognathus, Haematopinus, Solenoptes, Trichodectes*, and *Felicola*. The ectoparasites treated include but are not limited to fleas, ticks, mites, mosquitoes, flies, lice, blowfly and combinations thereof.

The compounds of formula I are especially useful for combating endoparasites. Endoparasites against which the compounds of formula I are active include those helminths such as *Anaplocephala, Ancylostoma, Anecator, Ascaris, Capillaria, Cooperia, Dipylidium, Dirofilaria, Echinococcus, Enterobius, Fasciola, Haemonchus, Oesophagostumum, Ostertagia, Toxocara, Strongyloides, Toxascaris, Trichinella, Trichuris*, and *Trichostrongylus*.

The compounds of formula I are especially useful for combating parasites of the following orders and species, respectively:

from the order of Isopoda, for example *Oniscus asellus, Armadillidium vulgare* and *Porcellio scaber;* from the order of Chilopoda, for example *Geophilus carpophagus* and *Scutigera* spp.;

from the order of Symphyla, for example *Scutigerella immaculate;* from the order of Collembola, for example *Onychiurus armatus;* from the order of Hymenoptera, for example *Diprion* spp., *Hoplocampa* spp., *Lasius* spp., *Monomorium pharaonis* and *Vespa* spp.;

from the class of Bivalva, for example, *Dreissena* spp.;

from the order of Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.;

fleas (Siphonaptera), e.g. *Ctenocephalides felis, Ctenocephalides canis, Xenopsylla cheopis* and *Ceratophyllus, Pulex irritans, Tunga penetrans*, and *Nosopsyllus fasciatus;* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis;* flies, mosquitoes (Diptera), e.g. *Aedes* spp., such as *Aedes aegypti, Aedes albopictus, Aedes vexans, Anastrepha ludens, Anopheles* such as *Anopheles maculipennis, Bibio hortulanus, Anopheles crucians, Anopheles albimanus, Anopheles gambiae, Anopheles freeborni, Anopheles leucosphyrus, Anopheles minimus, Anopheles quadrimaculatus, Calliphora erythrocephala, Calliphora vicina, Chrysomya bezziana, Chrysomya hominivorax, Chrysomya macellaria, Chrysops discalis, Chrysops silacea, Chrysops atlanticus, Cochliomyia* spp. such as *Cochliomyia hominivorax, Cordylobia anthropophaga, Culicoides furens, Culex* spp. such as *Culex pipiens, Culex nigripalpus, Culex quinquefasciatus, Culex tarsalis, Culiseta inornata, Culiseta melanura, Dermatobia hominis, Fannia* spp. such as *Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma* spp. such as *Hypoderma lineata, Leptoconops torrens, Lucilia caprina, Lucilia* spp. such as *Lucilia cuprina, Lucilia sericata, Lycoria pectoralis, Mansonia* spp., *Musca* spp. such as *Musca domestica, Muscina stabulans, Oestrus* spp. such as *Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys* spp. such as *Stomoxys calcitrans, Tabanus* spp. such as *Tabanus bovinus, Tabanus atratus, Tabanus lineola*, and *Tabanus similis, Ceratitis capitata, Chrysomyia* spp., *Cuterebra* spp., *Dacus oleae, Drosophila* spp., *Gastrophilus* spp., *Hylemyia* spp., *Hyppobosca* spp., *Liriomyza* spp., *Nezara* spp., *Oscinella frit, Pegomyia hyoscyami, Phorbia* spp., *Tannia* spp., *Tipula paludosa, Wohlfahrtia* spp.;

from the class of Gastropoda, for example, *Anion* spp., *Biomphalaria* spp., *Bulinus* spp., *Deroceras* spp., *Galba* spp., *Lymnaea* spp., *Oncomelania* spp., *Succinea* spp.;

from the order of Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.;

lice (Phthiraptera), e.g. *Damalinia* spp., *Haematopinus* spp., *Linognathus* spp., *Pediculus* spp., *Trichodectes* spp., *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus;* ticks and parasitic mites (Parasitiformes): ticks (Ixodida), e.g. *Ixodes scapularis, Ixodes holocyclus, Ixodes pacificus,*

*Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae;*

Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp;

from the class of Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici;*

Bugs (Heteropterida): *Cimex lectularius, Cimex hemipterus, Reduvius senilis, Triatoma* spp., *Rhodnius* ssp., *Panstrongylus* ssp. and *Arilus critatus;*

Anoplurida, e.g. *Haematopinus* spp., *Linognathus* spp., *Pediculus* spp., *Phtirus* spp., and *Solenopotes* spp;

Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp;

Roundworms Nematoda:

Whipworms and Trichinosis (Trichosyringida), e.g. Trichinellidae (*Trichinella* spp.) such as *Trichinella spiralis, Trichinella nativa, Trichinella britovi, Trichinella nelsoni, Trichinella pseudopsiralis,* (Trichuridae) *Trichuris* spp. such as *Trichuris trichuria, Capillaria* spp;

Rhabditida, e.g. *Rhabditis* spp, *Strongyloides* spp., *Helicephalobus* spp;

Strongylida, e.g. *Strongylus* spp., *Ancylostoma* spp., *Necator americanus, Bunostomum* spp. (Hookworm), *Trichostrongylus* spp., *Haemonchus* spp. such as *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma renale;* from the class of helminths, for example, *Ancylostoma duodenale, Ancylostoma ceylanicum, Acylostoma braziliensis, Dictyocaulus filaria, Diphyllobothrium latum, Echinococcus granulosus, Echinococcus multilocularis, Heterakis* spp., *Hymenolepis nana, Hyostrongulus* spp., *Loa Loa, Opisthorchis* spp., *Onchocerca volvulus, Schistosomen* spp., *Strongyloides fuelleborni, Strongyloides stercoralis, Strongyloides* spp., *Taenia saginata, Taenia solium, Trichostrongylus* spp.;

from the order of Homoptera, for example, *Acyrthosiphon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma pini, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginate, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii;* from the order of Isoptera, for example, *Reticulitermes* spp., *Odontotermes* spp.;

from the order of Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.;

from the order of Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria;* from the order of Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.;

from the class of Protozoa, for example, *Eimeria* spp.;

Intestinal roundworms (Ascaridida), e.g. *Ascaris* spp. such as *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi;*

Camallanida, e.g. *Dracunculus medinensis* (guinea worm)

Spirurida, e.g. *Thelazia* spp. *Wuchereria* spp. such as *Wuchereria bancrofti*, *Brugia* spp. such as *Brugia malayi*, *Brugia timori*, *Onchocerca* spp., *Dirojilari* spp. a, *Dipetalonema* spp., *Setaria* spp., *Elaeophora* spp., *Spirocerca lupi*, and *Habronema* spp.;

Thorny headed worms (Acanthocephala), e.g. *Acanthocephalus* spp., *Macracanthorhynchus hirudinaceus* and *Oncicola* spp;

Planarians (Plathelminthes):

Flukes (Trematoda), e.g. *Faciola* spp., *Fascioloides magna*, *Paragonimus* spp., *Dicrocoelium* spp., *Fasciolopsis buski*, *Clonorchis* spp. such as *Clonorchis sinensis*; *Schistosoma* spp., *Trichobilharzia* spp., *Alaria alata*, *Paragonimus* spp., and *Nanocyetes* spp;

Cercomeromorpha, in particular Cestoda (Tapeworms), e.g. *Diphyllobothrium* spp., *Tenia* spp., *Echinococcus* spp., *Dipylidium caninum*, *Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula I and compositions containing them are particularly useful for the control of pests from the orders Diptera, Siphonaptera and Ixodida.

Moreover, the use of the compounds of formula I and compositions containing them for combating mosquitoes is especially preferred.

The use of the compounds of formula I and compositions containing them for combating flies is a further preferred embodiment of the present invention.

Furthermore, the use of the compounds of formula I and compositions containing them for combating fleas is especially preferred.

The use of the compounds of formula I and compositions containing them for combating ticks is a further preferred embodiment of the present invention.

The compounds of formula I also are especially useful for combating endoparasites (including, but not limited to, nematodes, cestodes, trematodes, and protozoa).

The compounds of formula I can be effective through both contact (via soil, glass, wall, bed net, carpet, blankets or animal parts) and ingestion (e.g. baits).

The present invention relates to the therapeutic and the non-therapeutic use of compounds of formula I for controlling and/or combating parasites in and/or on animals.

The compounds of formula I may be used to protect the animals from attack or infestation by parasites by contacting them with a parasitically effective amount of compounds of formula I. As such, "contacting" includes both direct contact (applying the compounds/compositions directly on the parasite, e.g. also at its locus, and optionally also administrating the compounds/composition directly on the animal) and indirect contact (applying the compounds/compositions to the locus of the parasite). The contact of the parasite through application to its locus is an example of a non-therapeutic use of compounds of formula I.

"Locus" as defined above means the habitat, food supply, breeding ground, area, material or environment in which a parasite is growing or may grow outside of the animal. The compounds of the invention can also be applied preventively to places at which occurrence of the pests or parasites is expected.

The administration to the animal can be carried out both prophylactically and therapeutically. Administration of the active compounds is carried out directly or in the form of suitable preparations, orally, topically/dermally or parenterally.

For oral administration to warm-blooded animals, the formula I compounds may be formulated as animal feeds, animal feed premixes, animal feed concentrates, pills, solutions, pastes, suspensions, drenches, gels, tablets including chewable tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on, spray-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Pour-on formulations are described in U.S. Pat. No. 6,010,710, which is hereby incorporated herein by reference. The pour-on formulations may be advantageously oily, and generally comprise a diluent or vehicle and also a solvent (e.g. an organic solvent) for the active ingredient if the latter is not soluble in the diluent.

Spot-on formulations are described in U.S. Pat. Nos. 6,395,765; 6,867,229 6,096,329; 6,426,333, and 6,685,954, the disclosures of which are hereby incorporated herein by reference in their entirety.

Suitable preparations include without limitation:
Solutions such as oral solutions, concentrates for oral administration after dilution, solutions for use on the skin or in body cavities, pouring-on formulations, gels;
Emulsions and suspensions for oral or dermal administration; semi-solid preparations;
Formulations in which the active compound is processed in an ointment base or in an oil-in-water or water-in-oil emulsion base;
Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent or carrier and optionally adding further ingredients such as acids, bases, buffer salts, preservatives, and solubilizers. The solutions may be filtered and filled sterile.

Suitable solvents are physiologically tolerable solvents such as water, and organic solvents including alkanols such as ethanol, butanol, isopropanol, benzyl alcohol, glycerol, propylene glycol, polyethylene glycols, N-methyl-pyrrolidone, 2-pyrrolidone, and mixtures thereof. Other suitable solvents include, but are not limited to, acetyltributyl citrate, fatty acid esters such as the dimethyl ester, diisobutyl adipate, acetone, acetonitrile, butyl diglycol, dimethylacetamide, dimethylformamide, dipropylene glycol n-butyl ether, ethylene glycol monoethyl ether, ethylene glycol monomethyl ether, monomethylacetamide, dipropylene glycol monomethyl ether, liquid polyoxyethylene glycols, diethylene glycol monoethyl ether, ethylene glycol and diethyl phthalate, or a mixture of at least two of these solvents.

The active compounds can optionally be dissolved in physiologically tolerable vegetable or synthetic oils which are suitable for injection.

As vehicle or diluent, mention may be made of plant oils such as, but not limited to soybean oil, groundnut oil, castor oil, corn oil, cotton oil, olive oil, grape seed oil, sunflower oil, coconut oils etc.; mineral oils such as, but not limited to, petrolatum, paraffin, silicone, etc.; aliphatic or cyclic hydrocarbons or alternatively, for example, medium-chain (such as $C_8$-$C_{12}$) triglycerides.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

In some embodiments for topical compositions, the composition can be in ready-to-use solution form as is described, for example, in U.S. Pat. No. 6,395,765, which is incorporated herein by reference. In addition to the active agent compound, the ready-to-use solution can contain a crystallization inhibitor, an organic solvent and an organic co-solvent.

In some embodiments, the crystallization inhibitor can be present in a proportion of about 1 to about 30% (w/v). Typically, the crystallization inhibitor may be present in a proportion of about 1% to about 20% (w/v) or about 5% to about 15% (w/v). Acceptable inhibitors are those whose addition to the formulation inhibits the formation of crystals when the formulation is applied. In some embodiments, formulations may include compounds that function as crystallization inhibitors other than those listed herein. In these embodiments, the suitability of a crystallization inhibitor may be determined by testing if it will sufficiently inhibit the formation of crystals so that a sample containing 10% (w/v) of the compound of formula I in a solvent as described above with 10% (w/v) of the crystallization inhibitor will result in less 20, preferably less than 10 crystals when placed on a glass slide at 20° C. for 24 hours.

Crystallization inhibitors which are useful for the invention include but are not limited to:

(a) polyvinylpyrrolidone, polyvinyl alcohols, copolymers of vinyl acetate and of vinylpyrrolidone, 2-pyrrolidone including N-methylpyrrolidone, dimethylsufoxide, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and polymers derived from acrylic monomers, a solvent as described herein that inhibits the crystallization of the active agent, and others;

(b) anionic surfactants, such as alkaline stearates (e.g. sodium, potassium or ammonium stearate); calcium stearate or triethanolamine stearate; sodium abietate; alkyl sulfates, which include but are not limited to sodium lauryl sulfate and sodium cetyl sulfate; sodium dodecylbenzenesulphonate or sodium dioctyl sulphosuccinate; or fatty acids (e.g. coconut oil);

(c) cationic surfactants, such as water-soluble quaternary ammonium salts of formula N⁺R'R"R'"R""Y⁻, in which the R radicals are identical or different optionally hydroxylated hydrocarbon radicals and Y⁻ is an anion of a strong acid, such as halide, sulfate and sulphonate anions; cetyltrimethylammonium bromide is one of the cationic surfactants which can be used;

(d) amine salts of formula NR'R"R'", in which e R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine; or (g) a mixture of at least two of the compounds listed in (a)-(f) above.

Oral solutions are administered directly. Concentrates are administered orally after prior dilution to the use concentration. Oral solutions and concentrates are prepared according to the state of the art and as described above for injection solutions, sterile procedures not being necessary.

In one embodiment of the invention, the composition may be in paste form. Examples of embodiments in a paste form include but are not limited to those described in U.S. Pat. Nos. 6,787,342 and 7,001,889 (each of which are incorporated herein by reference).

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents include polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketones such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners include inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed include the thickeners given above.

Pour-on formulations are poured or sprayed onto limited areas of the skin, the active compound penetrating the skin and acting systemically.

Pour-on formulations may be prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which include water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methylpyrrolidone, 2-pyrrolidone, 2,2-dimethyl-4-oxy-methylene-1,3-diox-olane and glycerol formal.

Suitable colorants include all colorants permitted for use on animals and which can be dissolved or suspended.

Suitable absorption-promoting substances include, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants include sulfites or metabisulfites such as potassium metabisulfite, ascorbic acid, butylhydroxytoluene, butylhydroxyanisole, and tocopherol.

Suitable light stabilizers include, for example, novantisolic acid.

Suitable adhesives include, for example, cellulose derivatives, starch derivatives, polyacrylates, natural polymers such as alginates, gelatin.

Emulsions can be administered orally, dermally or as injections. Emulsions are either of the water-in-oil type or of the oil-in-water type. They may prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) include liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers include non-ionic surfactants, e.g. polyethoxylated castor oil, polyethoxylated sorbitan monooleate, sorbitan monostearate, glycerol monostearate, polyoxyethyl stearate, alkylphenol polyglycol ether; ampholytic surfactants such as disodium N-lauryl-p-iminodipropionate or lecithin; anionic surfactants, such as sodium lauryl sulfate, fatty alcohol ether sulfates, mono/dialkyl polyglycol ether orthophosphoric acid ester monoethanolamine salt; and cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They may be prepared by suspending the active compound in a suspending agent, if appropriate with addition of other auxiliaries such as wetting agents, colorants, bioabsorption-promoting substances, preservatives, antioxidants, light stabilizers.

Liquid suspending agents include all homogeneous solvents and solvent mixtures.

Suitable wetting agents (dispersants) include the emulsifiers given above.

Other auxiliaries which may be mentioned include those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients include all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries include the preservatives, antioxidants, and/or colorants which have been mentioned above.

Other suitable auxiliaries include lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formula I.

In some embodiments, it is favorable to apply the compounds of formula I in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use typically contain the compounds acting against ectoparasites in concentrations of 0.5 to 90 percent by weight, preferably of 1 to 50 percent by weight.

Furthermore, the preparations typically comprise the compounds of formula I against endoparasites in concentrations of 10 ppm to 2 percent by weight, preferably of 0.05 to 0.9 percent by weight, very particularly preferably of 0.005 to 0.25 percent by weight.

The effective amount of the endectocide in a dose may be selected from a range of between about 0.1 mg/kg and about 200 mg/kg or from about 1 to about 200 mg/kg of animal weight.

The veterinary compositions comprising the compounds of the present invention may optionally also comprise at least one other relevant parasiticidal ingredient, such as an insecticide, acaricide, parasiticide, etc.

The other parasiticide may be an endectocidal parasiticide of macrocyclic lactone type. This macrocyclic lactone type parasiticide includes but is not limited to avermectins and derivatives thereof, which includes but is not limited to abamectin, dimadectin, doramectin, emamectin, eprinomectin, ivermectin, latidectin, lepimectin, selamectin, and milbemycin and derivatives thereof including but not limited to milbemectin, moxidectin, nemadectin and milbemycin D.

The avermectin and milbemycin series of compounds are potent anthelmintic and antiparasitic agents against a wide range of internal and external parasites. The compounds which belong to this series are either natural products or are semi-synthetic derivatives thereof. The structure of these two series of compounds are closely related and they both share a complex 16-membered macrocyclic lactone ring; however, the milbemycin do not contain the aglycone substituent in the 13-position of the lactone ring. The natural product avermectins are disclosed in U.S. Pat. No. 4,310,519 to Albers-Schonberg, et al., and the 22,23-dihydro avermectin compounds are disclosed in Chabala, et al., U.S. Pat. No. 4,199,569. For a general discussion of avermectins, which include a discussion of their uses in humans and animals, see "Ivermectin and Abamectin," W. C. Campbell, ed., Springer-Verlag, New York (1989). Naturally occurring milbemycins are described in Aoki et al., U.S. Pat. No. 3,950,360 as well as in the various references cited in "The Merck Index" 12$^{th}$ ed., S. Budavari, Ed., Merck & Co., Inc. Whitehouse Station, N.J. (1996). Semisynthetic derivatives of these classes of compounds are well known in the art and are described, for example, in U.S. Pat. No. 5,077,308, U.S. Pat. No. 4,859,657, U.S. Pat. No. 4,963,582, U.S. Pat. No. 4,855,317, U.S. Pat. No. 4,871,719, U.S. Pat. No. 4,874,749, U.S. Pat. No. 4,427,663, U.S. Pat. No. 4,310,519, U.S. Pat. No. 4,199,569, U.S. Pat. No. 5,055,596, U.S. Pat. No. 4,973,711, U.S. Pat. No. 4,978,677, and U.S. Pat. No. 4,920,148, all of which are incorporated herein by reference in their entirety. Especially preferred compounds include ivermectin, emamectin, abamectin, doramectin, emamectin, eprinomectin, moxidectin and selamectin.

Another class of compounds that may be included in the inventive formulations or methods is insect growth regulators (IGR). Compounds belonging to this group are well known to the practitioner and represent a wide range of different chemical classes. These compounds all act by interfering with the development or growth of the insect pests. Compounds with an ovicidal and/or larvicidal effect on the immature stages of various ectoparasites are already known, for example from U.S. Pat. No. 5,439,924. Among these compounds described are those IGR compounds which act either by blocking the development of the immature stages (eggs and larvae) into adult stages, or by inhibiting the synthesis of chitin. Insect growth regulators are described, for example, in U.S. Pat. No. 3,748,356; U.S. Pat. No. 3,818,047; U.S. Pat. No. 4,225,598; U.S. Pat. No. 4,798,837; and U.S. Pat. No. 4,751,225, as well as in EP 179,022 or U.K. 2,140,010, the disclosures of which are hereby incorporated by reference in their entirety. French Patent No. A-2,713,889, which is hereby incorporated by reference, which generally describes an IGR combination comprising at least one compound with juvenile hormone activity and chitin synthesis inhibitors, with at least one of three N-aryldiazole compounds, in particular fipronil, to control many harmful insects belonging to very varied orders.

Examples of IGR which may be used in the veterinary formulations of the present invention include compounds which mimic juvenile hormones, in particular: Azadirchtin—Agridyne, Diofenolan, Fenoxycarb, Hydroprene, Kinoprene, Methoprene, Pyriproxyfen, Tetrahydroazadirachtin, 4-chloro-2-(2-chloro-2-methylpropyl)-5-(6-iodo-3-pyridylmethoxy)pyridizin-3(2H)-one, and chitin-synthesis inhibitors, in particular: chlorfluazuron, cyromazine, diflubenzuron, fluazuron, flucycloxuron, flufenoxuron, hexaflumuron, lufenuron, tebufenozide, teflubenzuron, triflumuron these compounds being defined by their international common name (The Pesticide Manual, 10$^{th}$ edition, 1994, Ed. Clive Tomlin, Great Britain). Chitin-synthesis inhibitors also include compounds such as 1-(2,6-difluorobenzoyl)-3-(2-fluoro-4-((trifluoromethyl)phenylurea, 1-(2,6-difluorobenzoyl)-3-(2-fluoro-4-(1,1,2,2-tetrafluoroethoxy)phenylurea and 1-(2,6-difluorobenzoyl)-3-(2-fluoro-4-trifluoromethyl) phenylurea. Novaluron is also an example of an IGR. Especially preferred IGR include methoprenes, pyriproxyfens, hydroprene, cyromazine, lufenuron, 1-(2,6-difluorobenzoyl)-3-(2-fluoro-4-(trifluoromethyl)phenylurea and novaluron.

Being part of another class of compounds the other parasiticide is an ectocidal parasiticide. Preferably the ectocidal parasiticide is an arylpyrazole. Examples of suitable arylpyrazoles are those described in EP 295 117 (U.S. Pat. Nos. 5,232,940, 5,547,974, 5,608,077, 5,714,191, 5,916,618 and 6,372,774), all of which are hereby incorporated herein by reference in their entirety. Further N-arylpyrazole compounds are described in U.S. Pat. Nos. 4,963,575; 5,885,607; 6,083,519; 6,010,710; 6,096,329 (6,685,954); EP 0 234 119, and EP 0 352 944; U.S. Pat. Nos. 5,817,688; 5,922,885; 5,994,386; 6,124,339; 6,180,798 and 6,395,906 and EP 0 780 378; U.S. Pat. No. 6,069,157 and EP 0 846 686; U.S. Pat. No. 6,350,771 and EP 0 948 485, all of which are hereby incorporated herein by reference in their entirety. The N-arylpyrazoles are known to possess excellent activity against insects, such as fleas and ticks. Fipronil is a specific type of N-aryl-pyrazole that is particularly effective against fleas and ticks, and is the active ingredient in Frontline® and Frontline Plus®.

For example, in the arylpyrazole molecule, the aryl group is attached to the pyrazole group at the 1-position of the pyrazole and the aryl group is a substituted phenyl group. Preferably, in the substituted phenyl group, the substitution is at the 2-, 4-, and/or 6-position of the phenyl ring and the substituents are selected from the group consisting of $C_1$-$C_4$ alkyl, halogen, and $C_1$-$C_4$-haloalkyl. More preferable the pyrazole is optionally substituted at the 3-position with a moiety selected from the group consisting of cyano, nitro, halogen, acetyl or formyl; is optionally substituted at the 4-position with Z—S(O)$_q$—, wherein Z is $C_1$-$C_4$ alkyl or $C_1$-$C_4$-haloalkyl and q is 0, 1 or 2; and is optionally substituted at the 5-position with an amino group or an amino substituted with $C_1$-$C_4$ alkyl or $C_1$-$C_4$ alkanoyl groups. Most preferably the arylpyrazole compound is 5-amino-1-[2,6-dichloro-4-(trifluoromethyl)phenyl]-4-[(trifluoromethyl) sulfinyl]-1H-pyrazole-3-carbonitrile ("fipronil"), pyriprole and pyrafluprole.

In one embodiment, the inventive compounds of formula I may be administered in combination with a compound of formula 2 shown below:

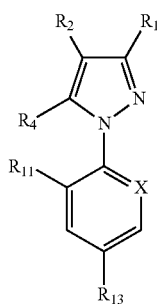

in which:

R$_1$ is alkyl, CN or halogen;
R$_2$ is S(O)$_n$R$_3$ or 4,5-dicyanoimidazol-2-yl or haloalkyl;
R$_3$ is alkyl or haloalkyl;
R$_4$ is a hydrogen, halogen, —NR$_5$R$_6$, —S(O)$_m$R$_7$, —C(O)R$_7$, —C(O)OR$_7$, alkyl, haloalkyl, —OR$_8$ or —N=C(R$_9$)(R$_{10}$);

R$_5$ and R$_6$ independently represent a hydrogen, alkyl, haloalkyl, —C(O)alkyl, —S(O)$_r$CF$_3$ or alkoxycarbonyl; or R$_5$ and R$_6$ can together form a divalent alkylene radical which is optionally interrupted by one or two divalent heteroatoms;

R$_7$ is an alkyl or haloalkyl;
R$_8$ is hydrogen, alkyl or haloalkyl;
R$_9$ is hydrogen or alkyl radical;
R$_{10}$ is an optionally substituted aryl or an optionally substituted heteroaryl group;
R$_{11}$ and R$_{12}$ represent, independently of one another, hydrogen, halogen CN or NO$_2$;
R$_{13}$ is a halogen, haloalkyl, haloalkoxy, S(O)$_q$CF$_3$ or SF$_5$ group;
m, n, q and r represent, independently of one another, an integer equal to 0, 1 or 2; and
X represents a trivalent nitrogen atom or a C—R$_{12}$ radical, the three other valencies of the carbon atom forming part of the aromatic ring.

Also contemplated are, for example, nodulisporic acid or nodulisporic acid derivatives. Nodulisporic acid and nodulisporic acid derivatives are known in the art as a class of compounds that are potent endo- and ectoantiparasitic agents. These compounds are based upon three structures, A, B or C, which have the following structures:

Nodulisporic Acid (Compound A)

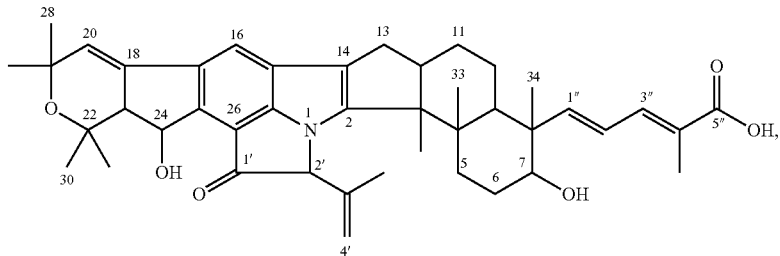

29,30-dihydro-20,30-oxa-nodulisporic acid (Compound B)

and 31-hydroxy-20,30-oxa-29,30,31,32-tetrahydro-nodulisporic acid (Compound C)

These nodulisporic acid compounds A, B and C were obtained from the fermentation culture of *Nodulisporium* sp. MF-5954 (ATCC 74245) and the isolation and purification of the three nodulisporic acids are disclosed in U.S. Pat. No. 5,399,582. Derivatives of these compounds are described in WO 96/29073 and U.S. Pat. Nos. 5,945,317; 5,962,499; 5,834,260; 6,399,796; 6,221,894; 6,136,838; 5,595,991; 5,299,582; and 5,614,546.

The compositions of the present invention also includes all nodulisporic acid derivatives know in the art, including all stereoisomers, such as those described in the prior publications described above, which are expressly incorporated by reference and described herein below in the following formulae. The substituents of those formulae are defined directly thereinafter, wherein their naming and definition is independently made from the compounds of the present invention and other compounds described above. Especially preferred are spot-on formulations comprising nodulisporic acid derivatives of the following formulae:

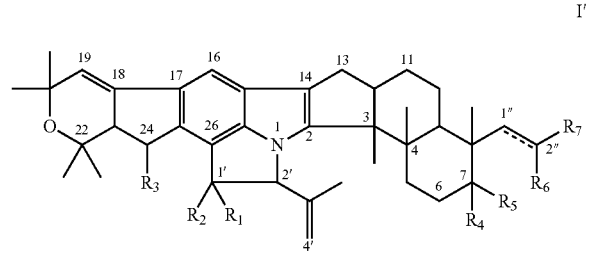

I' wherein $R_1$ is (1) hydrogen, (2) optionally substituted alkyl, (3) optionally substituted alkenyl, (4) optionally substituted alkynyl, (5) optionally substituted cycloalkyl, (6) optionally substituted cycloalkenyl, wherein the substituents on the alkyl, alkenyl, alkynyl, cycloalkyl and cycloalkenyl are 1 to 3 groups independently selected from (i) alkyl, (ii) $X-C_1-C_6$-alkyl, wherein X is O or S(O), (iii) cycloalkyl, (iv) hydroxy, (v) halogen, (vi) cyano, (vii) carboxy, (viii) $NY^1Y^2$, where $Y^1$ and $Y^2$ are independently H or alkyl, (ix) alkanoylamino, and (x) aroylamino wherein said aroyl is optionally substituted with 1 to 3 groups independently selected from $R^f$, (7) aryl or arylalkyl, wherein said aryl is optionally substituted with 1 to 3 groups independently selected from $R^f$, (8) perfluoroalkyl, (9) a 5- or 6-member heterocycle containing from 1 to 4 heteroatoms independently selected from oxygen, sulfur and nitrogen atoms optionally substituted by 1 to 3 groups independently selected from hydroxy, oxo, alkyl and halogen, and which may be saturated or partly unsaturated, $R_2$, $R_3$, and $R_4$ are independently $OR^a$, $OCO_2R^b$, $OC(O)NR^cR^d$; or $R_1$ and $R_2$ represent =O, =NOR$^a$ or =N—NR$^cR^d$; $R_5$ and $R_6$ are H; or $R_5$ and $R_6$ together represent —O—; $R_7$ is (1) CHO or the fragment (2)

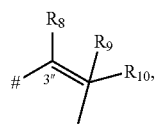

(2)

wherein # denotes the bond to the molecule of formula I', $R_8$ is (1) H, (2) $OR^a$ or (3) $NR^cR^d$, $R_9$ is (1) H or (2) $OR^a$, $R_{10}$ is (1) CN, (2) $C(O)OR^b$, (3) $C(O)N(OR^b)R^c$, (4) $C(O)NR^cR^d$, (5) NHC(O)$OR^b$, (6) NHC(O)NRCR$^d$, (7) $CH_2OR^a$, (8) $CH_2OCO_2R^b$, (9) $CH_2OC(O)NR^cR^d$, (10) $C(O)NR^cNR^cR^d$ or (11) $C(O)NR^cSO_2R^b$; and wherein ------ represents a single or a double bond, and wherein $R^a$ is (1) hydrogen, (2) optionally substituted alkyl, (3) optionally substituted alkenyl, (4) optionally substituted alkynyl, (5) optionally substituted alkanoyl, (6) optionally substituted alkenoyl, (7) optionally substituted alkynoyl, (8) optionally substituted aroyl, (9) optionally substituted aryl, (10) optionally substituted cycloalkanoyl, (11) optionally substituted cycloalkenoyl, (12) optionally substituted alkylsulfonyl, (13) optionally substituted cycloalkyl, (14) optionally substituted cycloalkenyl, wherein the substituents on the alkyl, alkenyl, alkynyl, alkanoyl, alkenoyl, alkynoyl, aroyl, aryl, cycloalkanoyl, cycloalkenoyl, alkylsulfonyl, cycloalkyl and cycloalkenyl are from 1 to 10 groups independently selected from hydroxy, alkoxy, cycloalkyl, arylalkoxy, $NR^gR^h$, $CO_2R_b$, $CONR^cR^d$ and halogen, (15) perfluoroalkyl, (16) arylsulfonyl optionally substituted with 1 to 3 groups independently selected from alkyl, perfluoroalkyl, nitro, halogen and cyano, or (17) a 5- or 6-member heterocycle containing 1 to 4 heteroatoms selected from oxygen, sulfur and nitrogen optionally substituted by 1 to 4 groups independently selected from alkyl, alkenyl, perfluoroalkyl, amino, $C(O)NR^cR^d$, cyano, $CO_2R^b$ and halogen, and which may be saturated or partly unsaturated; $R^b$ is (1) H, (2) optionally substituted aryl, (3) optionally substituted alkyl, (4) optionally substituted alkenyl, (5) optionally substituted alkynyl, (6) optionally substituted cycloalkyl, (7) optionally substituted cycloalkenyl, or (8) optionally substituted heterocycle containing from 1 to 4 heteroatoms independently selected from oxygen, sulfur and nitrogen; wherein the substituents on the aryl, alkyl, alkenyl, cycloalkyl, cycloalkenyl, heterocycle, or alkynyl are from 1 to 10 groups independently selected from (i) hydroxy, (ii) alkyl, (iii) oxo, (iv) $SO_2NR^gR^h$, (v) arylalkoxy, (vi) hydroxyalkyl, (vii) alkoxy, (viii) hydroxyalkoxy, (ix) aminoalkoxy, (x) cyano, (xi) mercapto, (xii) alkyl-S(O)$_m$, (xiii) cycloalkyl optionally substituted with 1 to 4 groups independently selected from $R^e$, (xiv) cycloalkenyl, (xv) halogen, (xvi) alkanoyloxy, (xvii) $C(O)NR^gR^h$, (xviii) $CO_2R^i$, (xix) formyl, (xx) —$NR^gR^h$, (xxi) 5- to 9-member heterocycle, which may be saturated or partially unsaturated, containing from 1 to 4 heteroatoms independently selected from oxygen, sulfur and nitrogen, and optionally substituted with 1 to 5 groups independently selected from $R^e$, (xxii) optionally substituted aryl, wherein the aryl substituents are 1,2-methylenedioxy or 1 to 5 groups independently selected from $R^e$, (xxiii) optionally substituted arylalkoxy, wherein the aryl substituents are 1,2-methylenedioxy or 1 to 5 groups independently selected from $R^e$, and (xxiv) perfluoroalkyl; $R^c$ and $R^d$ are independently selected from $R^b$; or $R^c$ and $R^d$ together with the N to which they are attached form a 3- to 10-member ring containing 0 to 2 additional heteroatoms selected from O, S(O)$_m$, and N, optionally substituted with 1 to 3 groups independently selected from $R^g$, hydroxy, thioxo and oxo; $R^e$ is (1) halogen, (2) alkyl, (3) perfluoroalkyl, (4) —S(O)$_mR^i$, (5) cyano, (6) nitro, (7) $R_{10}(CH_2)v-$, (8) $R^iCO_2(CH_2)v-$, (9) $R^{10}CO(CH_2)v-$, (10) optionally substituted aryl where the substituents are from 1 to 3 of halogen, alkyl, alkoxy, or hydroxy, (11) $SO_2NR^gR^h$, or (12) amino; $R^f$ is (1) alkyl, (2) $X-C_1-C_4$ alkyl, wherein X is O or S(O)$_m$, (3) alkenyl, (4) alkynyl, (5) perfluoroalkyl, (6) $NY^1Y^2$, where $Y^1$ and $Y^2$ are independently H or alkyl, (7) hydroxy, (8) halogen, and (9) alkanoylamino, $R^g$ and $R^h$ are independently (1) hydrogen, (2) alkyl optionally substituted with hydroxy, amino, or $CO_2R^i$, (3) aryl optionally substituted with halogen, 1,2-methylenedioxy, alkoxy, alkyl or perfluoroalkyl, (4) arylalkyl, wherein the aryl is optionally substituted with perfluorolkyl or 1,2-methylenedioxy; (5) alkoxycarbonyl, (6) alkanoyl, (7) alkanoylalkyl, (9) aryl alkoxycarbonyl, (10) aminocarbonyl, (11) monoalkylaminocarbonyl, (12) dialkylaminocarbonyl; or $R^g$ and $R^h$ together with the N to which they are attached form a 3- to 7-member ring containing 0 to 2 additional heteroatoms selected from O, S(O), and N, optionally substituted with 1 to 3 groups independently selected from $R^e$ and oxo; $R^i$ is (1) hydrogen, (2) perfluoroalkyl, (3) alkyl, (4) optionally substituted aryl or arylalkyl, where the aryl substituents are from 1 to 3 groups independently selected from halogen, alkyl, alkoxy, and hydroxy; m is 0 to 2; and v is 0 to 3; or a pharmaceutically acceptable salt thereof.

In a preferred embodiment, the present invention provides formulations comprising compounds of Formula I'

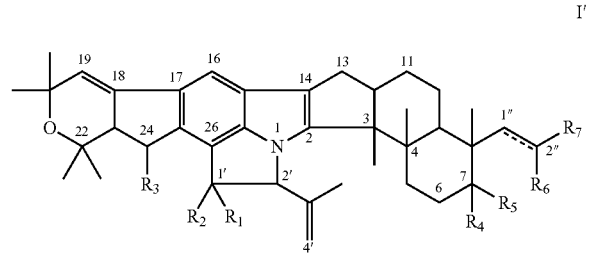

I' wherein $R_1$ is (1) hydrogen, (2) optionally substituted alkyl, (3) optionally substituted alkenyl, (4) optionally substituted alkynyl, (5) optionally substituted cycloalkyl, (6) optionally substituted cycloalkenyl where the substituents on the alkyl, alkenyl, alkynyl, cycloalkyl and cycloalkenyl are 1 to 3 groups independently selected from (i) alkyl, (ii) X—$C_1$-$C_6$-alkyl, where X is O or S(O)$_m$, (iii) cycloalkyl, (iv) hydroxy, (v) halogen, (vi) cyano, (vii) carboxy, and (viii) $NY^1Y^2$, where $Y^1$ and $Y^2$ are independently H or alkyl, (7) aryl or arylalkyl wherein said aryl is optionally substituted with 1 to 3 groups independently selected from $R^f$, (8) perfluoroalkyl, (9) a 5- or 6-member heterocycle containing from 1 to 4 heteroatoms independently selected from oxygen, sulfur and nitrogen atoms optionally substituted by 1 to 3 groups independently selected from hydroxy, oxo, alkyl and halogen, and which may be saturated or partly unsaturated, $R_2$, $R_3$, and $R_4$ are independently $OR^a$, $OCO_2R^b$, $OC(O)NR^cR^d$; or $R_1$ and $R_2$ represent =O, =$NOR^a$ or =N—$NR^cR^d$; $R_5$ and $R_6$ are H; or $R_5$ and $R_6$ together represent —O—; $R_7$ is (1) CHO or the fragment (2)

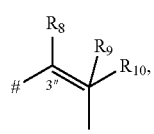

(2)

wherein

\# denotes the bond to the molecule of formula I'$R_8$ is (1) H, (2) OH, or (3) $NH_2$; $R_9$ is (1) H or (2) OH; $R_{10}$ is (1) C(O)$OR^b$, (2) C(O)N($OR^b$)$R^c$, (3) C(O)$NR^cR^d$, (4) NHC(O)$OR^b$, (5) NHC(O)$NR^cR^d$, (6) $CH_2OR^a$, (7) $CH_2OCO_2R^b$, (8) $CH_2OC(O)NR^cR^d$, (9) C(O)$NR^cNR^cR^d$, or (10) C(O)$NR^cSO_2R^b$; $R^a$ is (1) hydrogen, (2) optionally alkyl, (3) optionally substituted alkenyl, (4) optionally substituted alkynyl, (5) optionally substituted alkanoyl, (6) optionally substituted alkenoyl, (7) optionally substituted alkynoyl, (8) optionally substituted aroyl, (9) optionally substituted aryl, (10) optionally substituted cycloalkanoyl, (11) optionally substituted cycloalkenoyl, (12) optionally substituted alkylsulfonyl (13) optionally substituted cycloalkyl (14) optionally substituted cycloalkenyl where the substituents on the alkyl, alkenyl, alkynyl, alkanoyl, alkenoyl, alkynoyl, aroyl, aryl, cycloalkanoyl, cycloalkenoyl, alkylsulfonyl, cycloalkyl and cycloalkenyl are from 1 to 10 groups independently selected from hydroxy, alkoxy, cycloalkyl, aryl alkoxy, $NR^gR^h$, $CO_2R^b$, $CONR^cR^d$ and halogen, (15) perfluoroalkyl, (16) arylsulfonyl optionally substituted with 1 to 3 groups independently selected from alkyl, perfluoroalkyl, halogen and cyano, (17) a 5- or 6-member heterocycle containing 1 to 4 heteroatoms selected from oxygen, sulfur and nitrogen optionally substituted by 1 to 4 groups independently selected from alkyl, alkenyl, perfluoroalkyl, amino, C(O)$NR^cR^d$, cyano, $CO_2R^b$ and halogen, and which may be saturated or partly unsaturated; $R^b$ is (1) H, (2) optionally substituted aryl, (3) optionally substituted alkyl, (4) optionally substituted alkenyl, (5) optionally substituted alkynyl, (6) optionally substituted cycloalkyl (7) optionally substituted cycloalkenyl, or (8) optionally substituted 5- to 10-memberheterocycle containing from 1 to 4 heteroatoms independently selected from oxygen, sulfur and nitrogen; where the substituents on the aryl, alkyl, alkenyl, cycloalkyl, cycloalkenyl, heterocycle, or alkynyl are from 1 to 10 groups independently selected from (i) hydroxy, (ii) $C_1$-$C_3$ alkyl, (iii) oxo, (iv) $SO_2NR^gR^h$, (v) aryl alkoxy, (vi) hydroxy alkyl, (vii) alkoxy, (viii) hydroxyalkoxy, (ix) aminoalkoxy, (x) cyano, (xi) perfluoroalkyl, (xii) alkyl-S(O)$_m$, (xiii) cycloalkyl optionally substituted with 1 to 4 groups independently selected from $R^e$, (xiv) cycloalkenyl, (xv) halogen, (xvi) alkanoyloxy, (xvii) C(O)$NR^gR^h$, (xviii) $CO_2R^i$, (xix) optionally substituted arylalkoxy, wherein the aryl substituents are 1,2-methylenedioxy or 1 to 5 groups independently selected from $R^e$, (xx) —$NR^gR^h$, (xxi) 5 to 6-member heterocycle, which may be saturated or partially unsaturated, containing from 1 to 4 heteroatoms independently selected from oxygen, sulfur and nitrogen, and optionally substituted with 1 to 5 groups independently selected from $R^e$, and (xxii) optionally substituted aryl, wherein the aryl substituents are 1,2-methylenedioxy or 1 to 5 groups independently selected from $R^e$; $R^e$ is (1) halogen, (2) alkyl, (3) perfluoroalkyl, (4) —S(O)$_m R^i$, (5) cyano, (6) amino, (7) $R^i$O($CH_2$)$_v$—, (8) $R^i CO_2(CH_2)_v$—, (9) $R^{10}CO(CH_2)_v$—, (10) optionally substituted aryl where the substituents are from 1 to 3 of halogen, alkyl, alkoxy, or hydroxy, or (11) $SO_2NR^gR^h$; $R^f$ is (1) methyl, (2) X—$C_1$-$C_2$ alkyl, where X is O or S(O)$_m$, (3) halogen, (4) acetylamino, (5) trifluoromethyl, (6) $NY^1Y^2$, where $Y^1$ and $Y^2$ are independently H or methyl, and (7) hydroxy; $R^g$ and $R^h$ are independently (1) hydrogen, (2) alkyl optionally substituted with hydroxy, amino, or $CO_2R^i$ (3) aryl optionally substituted with halogen, 1,2-methylenedioxy, alkoxy, alkyl or perfluoroalkyl, (4) arylalkyl, wherein the aryl is optionally substituted with perfluorolkyl or 1,2-methylenedioxy; (5) alkoxycarbonyl, (6) alkanoyl, (7) alkanoyl alkyl, (9) arylalkoxycarbonyl, (10) aminocarbonyl, (11) monoalkylaminocarbonyl(12)dialkylaminocarbonyl; or $R^g$ and $R^h$ together with the N to which they are attached form a 5- to 6-member ring containing 0 to 2 additional heteroatoms selected from O, S(O), and N, optionally substituted with 1 to 3 groups independently selected from $R^e$ and oxo; $R^i$ is (1) hydrogen, (2) perfluoroalkyl, (3) alkyl, (4) optionally substituted arylalkyl, where the aryl substituents are from 1 to 3 groups independently selected from halogen, alkyl, alkoxy, and hydroxyl.

In another preferred embodiment, the present invention provides compositions comprising compounds of Formula I'

I'

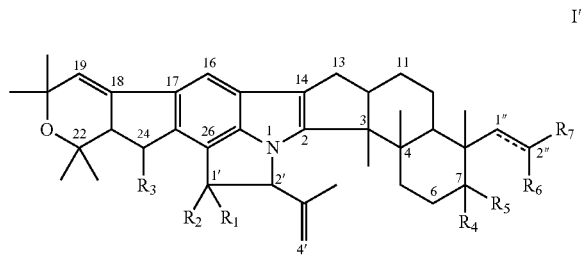

wherein $R^1$ is (1) hydrogen, (2) optionally substituted alkyl, (3) optionally substituted alkenyl, (4) optionally substituted alkynyl, where the substituents on the alkyl, alkenyl, and alkynyl are 1 to 3 groups independently selected from (i) methyl, (ii) X-methyl, wherein X is O or $S(O)_m$ and (iii) halogen, (5) aryl or arylalkyl wherein said aryl is optionally substituted with 1 to 3 groups independently selected from $R^f$, (6) trifluoromethyl; $R_2$, $R_3$, and $R_4$ are independently $OR^a$, $OCO_2R^b$, $OC(O)NR^cR^d$; or $R_1$ and $R_2$ represent =O, =$NOR^a$ or =N—$NR^cR^d$; $R_5$ and $R_6$ are H; or $R_5$ and $R_6$ together represent
—O—; $R_7$ is (1) CHO or the fragment (2)

(2)

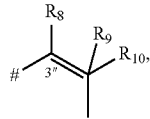

wherein # denotes the bond to the molecule of formula I; $R_8$ is (1) H, (2) OH, or (3) $NH_2R_9$ is (1) H, or (2) OH; $R_{10}$ is (1) $C(O)OR^b$, (2) $C(O)N(OR^b)R^c$, (3) $C(O)NR^cR^d$, (4) $NHC(O)OR^b$, (5) $NHC(O)NR^cR^d$, (6) $CH_2OR^a$, (7) $CH_2OCO_2R^b$, (8) $CH_2OC(O)NR^cR^d$, (9) $C(O)NR^cNR^cR^d$, or (10) $C(O)NR^cSO_2R^b$; $R^a$ is (1) hydrogen, (2) optionally substituted alkyl, (3) optionally substituted alkenyl, (4) optionally substituted alkynyl, (5) optionally substituted alkanoyl, (6) optionally substituted aroyl, (7) optionally substituted cycloalkanoyl, (8) optionally substituted cycloalkenoyl, (9) optionally substituted alkylsulfonyl where the substituents on the alkyl, alkenyl, alkynyl, alkanoyl, aroyl, cycloalkanoyl, cycloalkenoyl, and alkylsulfonyl, are from 1 to 5 groups independently selected from hydroxy, alkoxy, aryl alkoxy, $NR^gR^h$, $CO_2R^b$, $CONR^cR^d$ and halogen, (10) trifluoromethyl, (11) arylsulfonyl optionally substituted with 1 to 3 groups independently selected from methyl, trifluoromethyl and halogen, (12) a 5- or 6-member heterocycle containing 1 to 4 heteroatoms selected from oxygen, sulfur and nitrogen optionally substituted by 1 to 4 groups independently selected from methyl, trifluoromethyl, $C(O)NR^cR^d$, $CO_2R^b$ and halogen, and which may be saturated or partly unsaturated; $R_b$ is (1) H, (2) optionally substituted aryl, (3) optionally substituted alkyl, (4) optionally substituted alkenyl, (5) optionally substituted alkynyl, (6) optionally substituted cycloalkyl, (7) optionally substituted cycloalkenyl, or (8) optionally substituted 5- to 6-member-heterocycle containing from 1 to 4 heteroatoms independently selected from oxygen, sulfur and nitrogen; where the substituents on the aryl, alkyl, alkenyl, cycloalkyl, cycloalkenyl, heterocycle, or alkynyl are from 1 to 10 groups independently selected from (i) hydroxy, (ii) alkyl, (iii) oxo, (iv) $SO_2NR^gR^h$, (v) arylalkoxy, (vi) hydroxyalkyl, (vii) alkoxy, (viii) hydroxy alkoxy, (ix) amino alkoxy, (x) cyano, (xi) alkyl-$S(O)_m$, (xii) cycloalkyl optionally substituted with 1 to 4 groups independently selected from $R^e$, (xiii) cycloalkenyl, (xiv) halogen, (xv) alkanoyloxy, (xvi) $C(O)NR^gR^h$, (xvii) $CO_2R^i$, (xvii) —$NR^gR^h$, (xix) 5 to 6-member heterocycle, which may be saturated or partially unsaturated, containing from 1 to 4 heteroatoms independently selected from oxygen, sulfur and nitrogen, and optionally substituted with 1 to 5 groups independently selected from $R^e$, (xx) optionally substituted aryl, wherein the aryl substituents are 1,2-methylenedioxy or 1 to 5 groups independently selected from $R^e$, (xxi) optionally substituted aryl alkoxy, wherein the aryl substituents are 1,2-methylenedioxy or 1 to 5 groups independently selected from $R^e$, and (xxii) perfluoroalkyl; $R^e$ is (1) halogen, (2) alkyl, (3) perfluoroalkyl, (4) —$S(O)_mR^i$, (5) cyano, (6) $R^iO(CH_2)_v$—, (7) $R^iCO2(CH_2)_v$—, (8) $R_{10}CO(CH_2)_v$—, (9) optionally substituted aryl where the substituents are from 1 to 3 of halogen, alkyl, alkoxy, or hydroxy, (10) $SO_2NR^gR^h$, or (11) amino; $R^f$ is (1) methyl, (2) X—$C_1$-$C_2$ alkyl, where X is O or S(O), (3) trifluoromethyl, (4) $NY^1Y^2$, where $Y^1$ and $Y^2$ are independently H or methyl, (5) hydroxy, (6) halogen, and (7) acetylamino, $R^g$ and $R^h$ are independently (1) hydrogen, (2) alkyl optionally substituted with hydroxy, amino, or $CO_2R^i$(3) aryl optionally substituted with halogen, 1,2-methylenedioxy, alkoxy, alkyl or perfluoroalkyl, (4) arylalkyl, wherein the aryl is optionally substituted with perfluorolkyl or 1,2-methylenedioxy; (5) alkoxycarbonyl, (6) alkanoyl, (7) alkanoylalkyl, (9) arylalkoxycarbonyl, (10) aminocarbonyl, (11) monoalkylaminocarbonyl (12) dialkylaminocarbonyl; or $R^g$ and $R^h$ together with the N to which they are attached form a 5- to 6-membered ring containing 0 to 2 additional heteroatoms selected from O, S(O), and N, optionally substituted with 1 to 3 groups independently selected from $R^e$ and oxo; $R^i$ is (1) hydrogen, (2) perfluoroalkyl, (3) alkyl, (4) optionally substituted aryl or arylalkyl, where the aryl substituents are from 1 to 3 groups independently selected from halogen, alkyl, alkoxy, and hydroxy; and all other variables are as defined under Formula I' above.

Most especially preferred are formulations, wherein the composition comprises nodulisporic acid derivatives which are nodulisporamides, which are compounds of the following formula

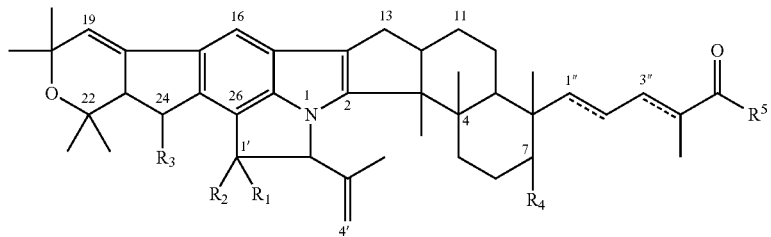

wherein $R_1$ is hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_8$ cycloalkyl, optionally substituted $C_5$-$C_8$ cycloalkenyl where the substituents on the alkyl, alkenyl, alkynyl, cycloalkyl and cycloalkenyl are 1 to 3 groups independently selected from $C_1$-$C_5$ alkyl, $C_1$-$C_{10}$ alkoxy, $C_1$-$C_{10}$ alkylthio, $C_1$-$C_{10}$ alkylsulfonyl, $C_3$-$C_8$ cycloalkyl, hydroxy, halogen, cyano, carboxy, amino, $C_1$-$C_{10}$ monoalkylamino, $C_1$-$C_{10}$ dialkylamino, $C_1$-$C_{10}$ alkanoyl amino and benzoyl amino wherein said benzoyl is optionally substituted with 1 to 3 groups independently selected from $C_1$-$C_4$ alkyl, $C_1$-$C_4$ alkoxy, $C_1$-$C_4$ alkylthio, $C_2$-$C_4$ alkenyl, $C_2$-$C_4$ alkynyl, $C_1$-$C_3$-perfluoroalkyl, amino, hydroxy, halogen, $C_1$-$C_5$ monoalkylamino, $C_1$-$C_5$ dialkylamino and $C_1$-$C_5$ alkanoyl amino, (7) phenyl $C_0$-$C_5$ alkyl wherein said phenyl is optionally substituted with 1 to 3 groups independently selected from $C_1$-$C_4$ alkyl, $C_1$-$C_4$ alkoxy, $C_1$-$C_4$ alkylthio, $C_2$-$C_4$ alkenyl, $C_2$-$C_4$ alkynyl, $C_1$-$C_3$-perfluoroalkyl, amino, hydroxy, carboxy, halogen, $C_1$-$C_5$ monoalkylamino, $C_1$-$C_5$ dialkylamino and $C_1$-$C_5$ alkanoyl amino, (8) $C_1$-$C_5$ perfluoroalkyl, (9) a 5- or 6-member ring selected from morpholino, pyridyl and piperazino, optionally substituted by 1 to 3 groups independently selected from hydroxy, oxo, $C_1$-$C_{10}$ alkyl and halogen, $R^2$, $R^3$, and $R^4$ are independently $OR^a$, $OCO_2R^b$, $OC(O)NR^cR^d$; or $R^1$ and $R^2$ together represent $=O$, $=NOR^a$ or $=N-NR^cR^d$; $R^5$ is $NR^cR^d$; $R^a$ is (1) hydrogen, (2) optionally substituted $C_1$-$C_{10}$ alkyl, (3) optionally substituted $C_3$-$C_{10}$ alkenyl, (4) optionally substituted $C_3$-$C_{10}$ alkynyl, (5) optionally substituted $C_1$-$C_{10}$ alkanoyl, (6) optionally substituted $C_1$-$C_{10}$ alkenyl, (7) optionally substituted $C_1$-$C_{10}$ alkynoyl, (8) optionally substituted benzoyl, (9) optionally substituted phenyl, (10) optionally substituted $C_1$-$C_7$ cycloalkanoyl, (11) optionally substituted $C_4$-$C_7$ cycloalkenoyl, (12) optionally substituted $C_1$-$C_{10}$ alkylsulfonyl (13) optionally substituted $C_3$-$C_8$ cycloalkyl (14) optionally substituted $C_5$-$C_8$ cycloalkenyl, where the substituents on the alkyl, alkenyl, alkynyl, alkanoyl, alkenoyl, alkynoyl, benzoyl, phenyl, cycloalkanoyl, cycloalkenoyl, alkylsulfonyl, cycloalkyl and cycloalkenyl are from 1 to 5 groups independently selected from hydroxy, $C_1$-$C_6$ alkoxy, $C_3$-$C_7$ cycloalkyl, aryl $C_1$-$C_3$ alkoxy, $NR^gR^h$, $CO_2R^b$, $CONR^cR^d$ and halogen, (15) $C_1$-$C_5$ perfluoroalkyl, (16) phenylsulfonyl optionally substituted with 1 to 3 groups independently selected from $C_1$-$C_5$ alkyl, $C_1$-$C_5$ perfluoroalkyl, nitro, halogen or cyano, (17) a 5- or 6-member ring selected from piperidino, morpholino, pyridyl and piperazino optionally substituted by 1 to 4 groups independently selected from $C_1$-$C_5$ alkyl, $C_1$-$C_5$ alkenyl, $C_1$-$C_5$ perfluoroalkyl, amino, $C(O)R^cR^d$, cyano, $CO_2R^b$ or halogen; $R^b$ is (1) H, (2) optionally substituted phenyl, (3) optionally substituted $C_1$-$C_{10}$ alkyl, (4) optionally substituted $C_3$-$C_{10}$ alkenyl, or (5) optionally substituted $C_3$-$C_{10}$ alkynyl, where the substituents on the phenyl, alkyl, alkenyl or alkynyl are from 1 to 5 groups independently selected from hydroxy, $C_1$-$C_6$ alkoxy, $C_3$-$C_7$ cycloalkyl, halogen, $C_1$-$C_5$ alkanoyloxy, $C(O)NR^cR^d$, $CO_2R^b$, formyl, $-NR^gR^h$, optionally substituted phenyl, and optionally substituted phenyl $C_1$-$C_3$ alkoxy, wherein the phenyl substituents are 1 to 3 groups independently selected from $R^e$; $R^c$ and $R^d$ are independently $R^b$; or $R^c$ and $R^d$ together with the N to which they are attached form a piperidino, morpholino or piperazino optionally substituted with 1 to 3 groups independently selected from $R^g$ and oxo; $R^e$ is (1) halogen, (2) $C_1$-$C_7$ alkyl, (3) $C_1$-$C_3$ perfluoroalkyl, (4) $-S(O)_mR^i$, (5) cyano, (6) nitro, (7) $R^jO(CH_2)_v-$, (8) $R^jCO_2(CH_2)_v-$, (9) $R^jOCO(CH_2)_v^-$, (10) optionally substituted phenyl where the substituents are from 1 to 3 halogen, $C_1$-$C_6$ alkyl, $C_1$-$C_6$ alkoxy, or hydroxy; v is 0 to 3; $R^g$ and $R^h$ are independently (1) hydrogen, (2) $C_1$-$C_6$ alkyl, (3) aryl, (4) aryl $C_1$-$C_6$ alkyl, (5) $C_1$-$C_5$ alkoxycarbonyl, (6) $C_1$-$C_5$ alkylcarbonyl, or (7) $C_1$-$C_5$ alkanoyl $C_1$-$C_5$ alkyl; or $R^g$ and $R^h$ together with the N to which they are attached form a piperidino, morpholino or piperazino optionally substituted with 1 to 3 groups independently selected from $R^g$ and oxo; $R^i$ and $R^j$ are independently (1) hydrogen, (2) $C_1$-$C_3$ perfluoroalkyl, (3) optionally substituted $C_1$-$C_6$ alkyl, where the substituents are aryl or substituted phenyl; (4) phenyl or substituted phenyl where the substituents are from 1 to 3 groups independently selected from halogen, $C_1$-$C_6$ alkyl, $C_1$-$C_6$ alkoxy, or hydroxy; m is 0 to 2; or a pharmaceutically acceptable salt thereof.

Most Especially Preferred are Compositions Comprising Compounds of the Formula

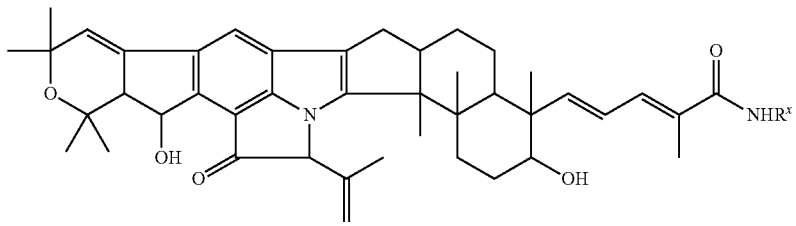

wherein $R^x$ is selected from the group consisting of H, $CH_3$, $CH_2CH_3$, $C(CH_3)_3$, $CH_2CH_2CH_3$, $CH_2CH_2OH$, $CH(CO_2CH_3)CH_2OH$, $CH_2CO_2CH_3$, $CH_2CH(OCH_2CH_3)_2$, $CH_2CH_2OCH_2CH_2OH$, $CH(CH_3)(CH_2)_3C(CH_3)_2OH$, $(CH_2)_3OH$, $(CH_2)_4OH$, $(CH_2)SOH$, $CH(CH_2OH)CH_2CH_3$, $NHC(CH_3)_3$, $CH_2CN$, $(CH_2)_6OH$, $CH_2CH(OH)CH_3$, $CH(CH_2OH)CH_2CH_2CH_3$, $CH_2CH_2SCH_3$, $CH_2CH_2SCH_2CH_3$, $CH_2CONH$, $CH(CH_3)(CH_2OH)_2$, $CH_2CH_2NHCH_2CH_2OH$, $CH(CH_2OH)(CH_2)_3CH_3$, $CH(CH_2OCH_3)CH_3$, $(CH_2)_2SH$, $(CH_2)_4NH_2$, $CH_2CH_2SO_2CH_3$, $CH_2CH_2S(O)CH_3$, $CH(CH(CH_3)_2)CH_2OH$, $(CH_2)_3NH_2$, $(CH_2)_3N(CH_2CH_3)_2$, $(CH_2)_3N(CH_3)_2$, $OCH_2CH_3$, $CH_2CH(OH)CH_2OH$, $OCH_3$, $CH_2CH_2OCH_3$, $CH_2CH_2NHC(O)CH_3$, $C(CH_3)_2CH_2OH$, c-$C_3H_5$, c-$C_6H_{11}$, $(CH_2)_3OCH_2CH_3$, $CH_2C\equiv CH_2$, $C(CH_2CH_3)(CH_2OH)_2$, $CH_2C\equiv CH$, $CH_2CO_2CH_2CH_3$, $CH_2CH_2F$, $(CH_2)_3OCH_2)_{11}$ $CH_3$, $CH_2CH_2N(CH_3)_2$, $CH_2CH_2OCH_2CH_2NH_2$, $CH_2CF_3$, $NHCH_2CO_2CH_2CH_3$, $CH(CH_3)CO_2CH_3$, $C(CH_3)_2\ CH_2C(O)CH_3$, $CH(CO_2CH_2CH_3)_2$, $CH_2CH_3$, $CH(CH_2CH_2CH_3)CO_2CH_3$, $CH_2CH_2CH_2OCH_3$, $C(CH_3)_2\ C\equiv CH$, $(CH_2)_4CH_3$, $CH(CH_2CH_2CH_3)_2$, $(CH_2)_5CH_3$, $CH_2CH_2CO_2H$, $CH(CH(CH_3)_2)CO_2CH_3$, $OCH_2CO_2H$, $CH(CH(CH_3)_2)CH_2OH$, $CH(CH(CH_3)_2)CH_2OH$, $CH(CH_3)CH_2OH$, $CH(CH_3)CH_2OH$, $CH(CH_3)_2$, $C(CH_3)_3$, $(CH_2)CH(CH_3)_2$, $CH(CH_3)CH_2CH_3$, $CH_2CH(CH_3)OH$, $(CH_2)_3CH_3$, $(CH_2)_2OCH_2CH_3$, 1-adamantyl, $(CH_2)_8CH_3$, $CH(CH_3)CH(CH_3)_2$, $(CH_2)_3NHCH_3$, $(CH_2)_2N(CH_2CH_3)_2$,

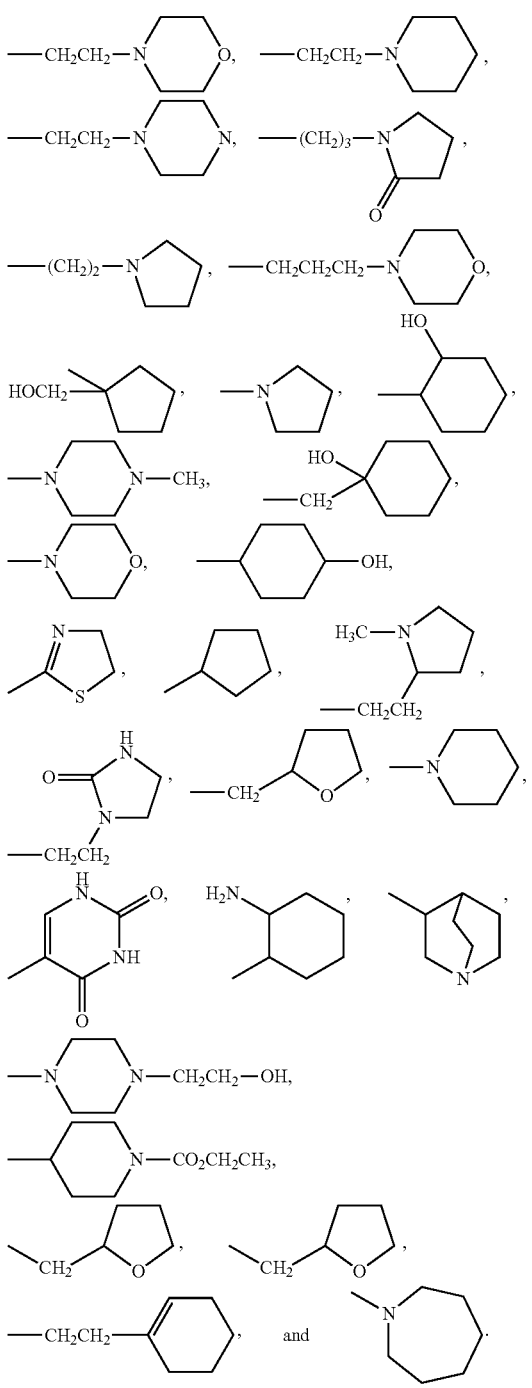

An especially preferred nodulisporamide compound for compositions for the inventive use is one wherein $R^x$ is with t-butyl (or "nodulisporamide").

In another embodiment of the invention, the compound of formula I may be administered in combination with a formamidine compound. The formamidine class of compounds include, but are not limited to, amitraz (Mitaban™, Pfizer; Point-Guard®, Intervet; Preventic®, Virbac; Taktic®, Intervet), chlordimeform, chloromebuform, formetanate and formparanate. Amitraz is a well-known acaracide/insecticide from the formamidine family acknowledged to be useful as a miticidal agent and for the control of ticks. See *Plumb's Veterinary Drug Handbook (Fifth Edition)*, ed. Donald C. Plumb, Blackwell Publishing, pg. 34, (2005). The formamidine family of pesticides is distinguished by a characteristic —N═CR—NR'— moiety. Amitraz differs from other members of the formamidine family in that there are two such moieties in the compound. Amitraz has the following structure:

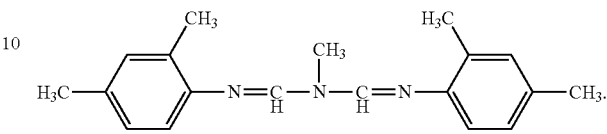

In one embodiment, the compound of formula I is administered in combination with one or more formamidine compounds of formula (3):

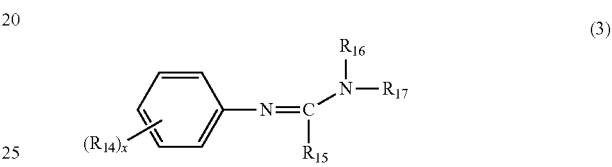

(3)

wherein:
x is an integer from 0-5;
$R_{14}$ is alkyl, halogen or —OC(═O)$NR_aR_b$, where $R_a$ and $R_b$ are independently hydrogen or alkyl;
  wherein $R_a$ and $R_b$ are independently hydrogen or alkyl;
$R_{15}$ is hydrogen or alkyl;
$R_{16}$ is hydrogen or alkyl;
$R_{17}$ is hydrogen, alkyl or

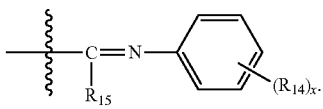

Other classes of compounds that may be administered in combination with the compounds of formula I include, but are not limited to, 2-acyl-4-oxo-pyrazino-isoquinoline derivatives, such as praziquantel or 1,4,5,6-tetrahydro-2-[2-substituted]vinyl pyrimidines and 2-[(2-substituted)vinyl]-2-imidazolines such as pyrantel (see U.S. Pat. No. 3,502,661, herein incorporated by reference.).

The proportions by weight of parasiticide of formula I to the additional parasiticide may be between about 5/1 and about 20,000/1.

The parasiticidal compound(s) of the present invention and the associated endectocidal parasiticide may be contained in a controlled- and sustained-release preparation, such as, for example, microspheres, granules or implants. This can be obtained, for example, by mixing a controlled-release preparation of an ectoparasiticide, such as fipronil, and/or a controlled-release preparation of endectocide, such as ivermectin, in a suitable vehicle, such as water, oil or a medium-chain triglyceride.

In such a controlled-release preparation, the formulations are preferably drawn up so as to release between 5 and 100 mg/kg/day, for example 45 mg/kg/day, of compound of formula I, and from 0.01 to 15 mg/kg/day of ectoparasiticide, for example fipronil, or, for example, 0.5 mg/kg/day of endectocide, for example ivermectin.

In the case of such controlled-release preparations, a dose for a treatment of very long duration of an animal will preferably comprise a compound of formula I and between 1 and 20 mg/kg of fipronil or between 2 mg/kg and 3 mg/kg of endectocide, in particular of ivermectin.

In a preferred embodiment of the present invention, the compositions comprising the compounds of formula I are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

The following synthetic and biological examples are offered to illustrate this invention and are not to be construed in any way as limiting the scope of this invention.

EXAMPLES

The present invention is now illustrated in further details by the following examples.

S. Synthesis Examples

S.1 Synthesis of (5-Chloro-thieno[2,3-d]pyrimidin-4-yl)-[(S)-1-(4-trifluoromethylsulfanyl-phenyl)-ethyl]-amine (Compound C.3-S)

Step 1: Synthesis of 2-Methyl-propane-2-(R)-sulfinic acid [1-(4-trifluoromethylsulfanyl-phenyl)-ethylidene]-amide (S.1)

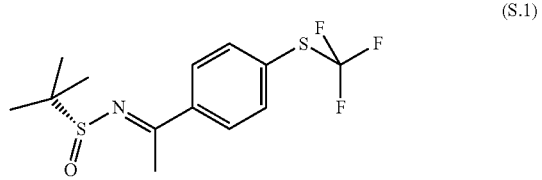 [SMILES: C/C(=N\[S@](=O)C(C)(C)C)c1ccc(SC(F)(F)F)cc1]

(S.1)

5.44 g (24.7 mmol) 4-(Trifluormethylthio)-acetophenone were dissolved in 100 ml THF, followed by addition of 9.33 ml (9.40 g; 41.2 mmol) Ti(OEt)$_4$. 2.50 g (20.6 mmol) (R)-(+)-2-Methyl-2-propansulfinamide were added portion wise. The mixture was stirred at 65° C. for 16 h. Upon cooling to room temperature, the solvent was removed and ethyl acetate was added to the residue. Water was added carefully. The precipitate was removed by filtration and washed thoroughly with ethyl acetate. The precipitate was discarded. For the filtrate, the layers were separated and the aqueous layer was extracted two times with ethyl acetate. The combined organic layers were dried over Na$_2$SO$_4$ and the solvent was removed to yield about 7 g crude product. The crude product was purified on silica (cyclohexane/ethyl acetate) to yield about 4.9 g of the desired product.

Step 2: 2-Methyl-propane-2-(R)-sulfinic acid [(S)-1-(4-trifluoromethylsulfanyl-phenyl)-ethyl]-amide (S.1)

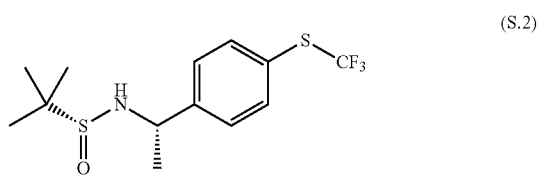 [SMILES: C[C@H](N[S@](=O)C(C)(C)C)c1ccc(SC(F)(F)F)cc1]

(S.2)

5.6 g (17.3 mmol) (4a) were dissolved in 60 ml THF and cooled to 0° C. 52 ml of a 1.0 M solution of L-selectride in THF were added slowly. Stirring was continued at this temperature for 30 min. The mixture was allowed to warm to room temperature and stirring was continued for 2 h.

Step 3: (S)-1-(4-Trifluoromethylsulfanyl-phenyl)-ethylamine (S.3)

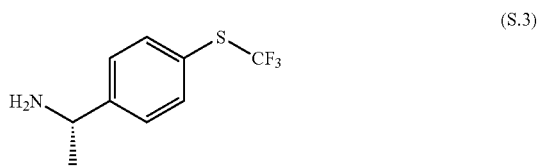

(S.3)

3.50 g (10.8 mmol) (S.2) were dissolved in 40 ml methanol and 5.4 ml (21.6 mmol) of a 4N HCl solution was added at 10 C via syringe. The cooling bath was removed and stirring was continued for 2 h at room temperature. The solvent was removed and water was added. The solution was extracted two times with dichloromethane. A basic pH was adjusted to the aqueous layer by addition of Na$_2$CO$_3$— solution and the aqueous layer was extracted three times with dichloromethane. The organic layers were combined and dried over Na$_2$SO$_4$. The solvent was removed to yield 2.27 g of a colourless oil. Enantiomeric analysis showed an enantiomeric ratio of >99:<1 in favour of the (S)-enantiomer.

Step 4: Synthesis of (5-Chloro-thieno[2,3-d]pyrimidin-4-yl)-[(S)-1-(4-trifluoromethyl-sulfanyl-phenyl)-ethyl]-amine (Compound C.3-S)

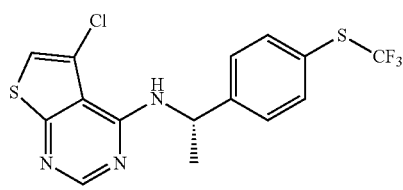 [SMILES: C[C@H](Nc1ncnc2scc(Cl)c12)c1ccc(SC(F)(F)F)cc1]

2.07 g (10.1 mmol) 4,4-Dichloro-thieno-[2,3-d]-pyrimidine, 0.94 g triethyl amine (9.2 mmol) and 155 mg (0.42 mmol) tetra-butyl ammonium iodide were mixed in 100 ml toluene. 1.85 g (8.4 mmol) (S.3) was added and the mixture was heated to reflux for 15 h. Upon cooling to room temperature, the solvent was removed and water was added to the residue. The aqueous layer was extracted three times with dichloromethane. The combined organic layers were washed subsequently with 1N HCl and water and dried over Na$_2$SO$_4$. The solvent was removed and the residue was purified on silica (cyclohexanes/ethyl acetate) to yield 2.37 g of Compound C.3-S.

Other compounds of formula I of the present invention can be prepared in analogy as described above in synthesis example.

C. Compound Examples

Some examples of the preferred compound for use in the methods according to the present invention are characterized by their physical data in the following table C.

The Compound examples were characterized e.g. by coupled High Performance Liquid Chromatography/mass spectrometry (HPLC/MS) or by their melting points.

Analytical HPLC column: RP-18 column Chromolith Speed ROD from Merck KgaA, Germany). Elution: acetonitrile+0.1% trifluoroacetic acid (TFA)/water+0.1% trifluoroacetic acid (TFA) in a ratio of from 5:95 to 95:5 in 5 minutes at 40° C.

TABLE C

| Compound example no. | Structure | Physico-chemical data: HPLC-MS: t$_r$ [min]; m/z or mp = melting point [° C.] |
|---|---|---|
| C.1 | 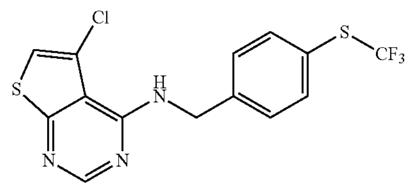 [SMILES: FC(F)(F)Sc1ccc(CNc2ncnc3scc(Cl)c23)cc1] | t$_r$ = 3.871 min. m/z: 376.05 g/mol |
| C.2 | 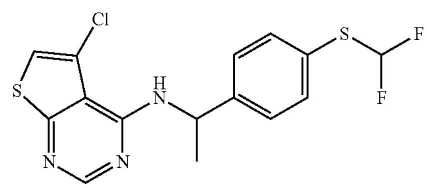 [SMILES: CC(Nc1ncnc2scc(Cl)c12)c1ccc(SC(F)F)cc1] | t$_r$ = 3.659 min. m/z: 371.70 g/mol |
| C.3 | 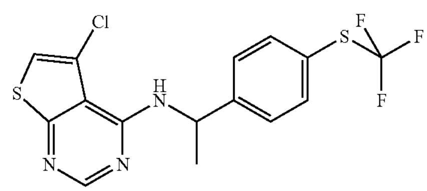 [SMILES: CC(Nc1ncnc2scc(Cl)c12)c1ccc(SC(F)(F)F)cc1] | t$_r$ = 4.231 min. m/z: 390.05 g/mol |
| C.3-R | 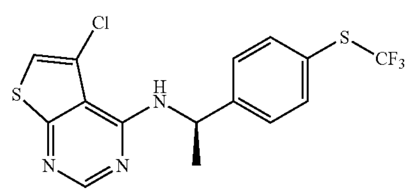 [SMILES: C[C@@H](Nc1ncnc2scc(Cl)c12)c1ccc(SC(F)(F)F)cc1] | t$_r$ = 4.231 min. m/z: 390.05 g/mol |
| C.3-S | 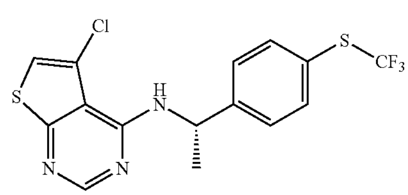 [SMILES: C[C@H](Nc1ncnc2scc(Cl)c12)c1ccc(SC(F)(F)F)cc1] | t$_r$ = 4.231 min. m/z: 390.05 g/mol |
| C.4 | 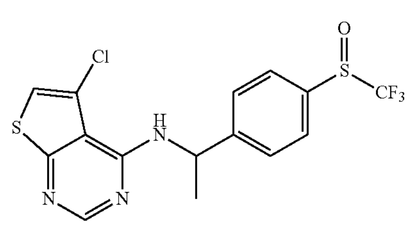 [SMILES: CC(Nc1ncnc2scc(Cl)c12)c1ccc(S(=O)C(F)(F)F)cc1] | t$_r$ = 3.283 min. m/z: 405.60 g/mol |

TABLE C-continued

| Compound example no. | Structure | Physico-chemical data: HPLC-MS: $t_r$ [min]; m/z or mp = melting point [° C.] |
|---|---|---|
| C.5 | (thieno[2,3-d]pyrimidine with Cl, NH-CH(CH3)-phenyl-S-CH2-CF3) | $t_r$ = 3.955 min. m/z: 404.15 g/mol |
| C.6 | (thieno[2,3-d]pyrimidine with Cl, NH-CH(CH3)-phenyl-S-CF2-CF3) | $t_r$ = 4.295 min. m/z: 439.60 g/mol |
| Comparative example CE.1 | (thieno[2,3-d]pyrimidine with Cl, NH-CH(CH3)-phenyl-S-CH3) | $t_r$ = 3.858 min. m/z: 335.80 g/mol |
| Comparative example CE.2 | (thieno[2,3-d]pyrimidine with Cl, NH-CH(CH3)-phenyl-O-CF3) | $m_p$ = 79-80° C. |

B. Biological Examples of Action Against Pests

Under general conditions, if not otherwise specified, most test solutions are prepared as follow: The active compound is dissolved at the desired concentration in a mixture of 1:1 (vol:vol) distilled water:acetone. The test solution is prepared at the day of use.

Test solutions are prepared in general at concentrations of 1000 ppm, 500 ppm, 300 ppm, 100 ppm and 30 ppm (wt/vol).

B.1 Cowpea Aphid (*aphis craccivora*)

Potted cowpea plants colonized with approximately 100-150 aphids of various stages were sprayed after the pest population has been recorded. Population reduction was assessed after 24, 72, and 120 hours.

In this test, compounds C.1, C.2, C.3, C.4, C.5 and C.6 showed at 300 ppm over 80% mortality in comparison with untreated controls.

B.2 Spider Mite (*Tetranychus* spp.)

Contact/Oral Activity:

Potted cotton plants colonized with approximately 50 mites of various stages are sprayed after the pest population has been recorded. Population reduction (or increase) after 24, 72, and 120 hours is assessed.

In this test, compounds C.3 and C.6 showed at 300 ppm over 80% mortality in comparison with untreated controls.

B.3 Rice Brown Plant Hopper (*Nilaparvata lugens*)

Rice seedlings were cleaned and washed 24 hours before spraying. The active compounds were formulated in 50:50 acetone:water (vol:vol) and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, compounds C.3 and C.6 showed at 300 ppm over 80% mortality in comparison with untreated controls.

B.4. Activity Against Yellow Fever Mosquito (*Aedes aegypti*)

The compounds were formulated in 100% DMSO and were tested in microtiter plates containing 180 ul 1× Luria Broth media and 10 neonate *A. aegypti* larvae. The efficacy of a compound was determined based on the motility of the larvae as compared to average motility of control wells containing DMSO only. Compounds with >80% reduction in motility at a concentration of 10 ppm were tested in a dose response assay to determine EC50 values.

In this test, compounds C.1, C.2, C.3, C.4, C.5 and C.6. showed an EC50 values of <1 ppm.

B.5. Activity in Rat Ectoparasiticide Model

Rats were infested with 50 *Ctenocephalides felis* fleas. Approximately twenty four hours later rats (3 per group) were treated topically with test compounds at doses of 20 mg/kg or 10 mg/kg body weight. Placebo (vehicle) and positive control groups were included in each study. Forty eight hours post-treatment, fleas were collected from each rat using a flea comb. The percent efficacy per treatment group was calculated using the following formula:

% efficacy = $100 \times (C-T)/C$ where C is the geometric mean of live fleas recovered in the placebo group and T is the geometric mean of live fleas recovered in the respective treatment group.

Compound C.3-S reduced flea counts by an average of 89% and 71% at doses of 20 mg/kg and 10 mg/kg, respectively (n=2 [number of replicas]).

CB. Comparative Biological Examples

The biological activity shown tables under CB.1 and CB.2 was evaluated on scale range from 0% as showing no biological activity to 100% as having total control. The biological tests were conducted as described above.

CB 1. Comparative Biological Test 1:

Compounds of the present invention showed surprisingly an unexpected higher biological activity in comparison to e.g comparative example CE.1 disclosed in WO 2006/047397 (therein compound no. 42) and comparative example CE.2 disclosed in WO2007/135029 (therein compound C.2).

TABLE CB.1.1

Activity of comparative compound CE.1

| Organism | Concentration In [ppm] | compound example C.3 activity in [%] | comparative example CE. 1 activity in [%] |
|---|---|---|---|
| Nilaparvata lugens | 300 | 100 | 0 |
| Spide mite | 300 | 90 | n.a.* |

*compound CE. 1 had an activity of 50% at 500 ppm

TABLE CB.1.2

Activity of comparative compound CE.2

| Organism | Concentration In [ppm] | compound example C.3 activity in [%] | comparative example CE. 2 activity in [%] |
|---|---|---|---|
| Spider mite | 300 | 90 | 50 |

CB.2 Comparative Biological Test 2:

For the compounds of the present invention, a higher biological activity could be further demonstrated for the S-enantiomers, also in comparison to stereoisomer compounds in the art (e.g comparative example CE.2 disclosed in WO2007/135029 (therein compound C.2).

TABLE CB.2.1

Activity of different stereoisomers

| Organism | Conc. In [ppm] | Stereoisomers of compound example 3 activity in [%] | | |
|---|---|---|---|---|
| | | C.3 | C.3-R | C.3-S |
| Nilaparvata lugens | 300 | 100 | 0 | 100 |
| Spider mite | 300 | 90 | 0 | 90 |
| Cow pea aphid | 300 | 100 | 0 | 100 |

| | | Activity at 1 [ppm] | | |
|---|---|---|---|---|
| | EC$_{50}$ | C.3 | C.3-R | C.3-S |
| Aedes aegypti | EC50 | 0.29 | 0 | 0.21 |

TABLE CB.2.2

Activity of stereoisomeric comparative compound CE.2

| Organism | Concentration In [ppm] | compound example C.3-S activity in [%] | comparative example CE.2 activity in [%] |
|---|---|---|---|
| Spider mite | 300 | 90 | 50 |

| | Dosage In [mg/kg] | Efficacy in [%] | |
|---|---|---|---|
| Ctenocephalides felis | 10 | 71 | 70 |
| | 20 | 89 | 82 |

We claim:

1. A 4-amino-thieno[2,3-d]-pyrimidine compound for combating or controlling insects, arachnids or nematodes of formula I:

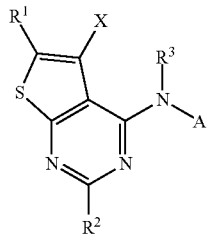

(formula I)

wherein

X is selected from halogen, $C_1$-$C_{10}$-alkyl or $C_1$-$C_{10}$-haloalkyl;

$R^1$ is selected from the group consisting of hydrogen, halogen, formyl, $C_1$-$C_{10}$-alkyl, $C_1$-$C_{10}$-alkenyl, $C_1$-$C_{10}$ alkynyl, $C_1$-$C_{10}$-haloalkyl, $C_1$-$C_{10}$-haloalkenyl, $C_1$-$C_{10}$-haloalkynyl, $C_1$-$C_{10}$-alkoxy, $C_1$-$C_6$-alkoxy-$C_1$-$C_6$-alkyl, $C_1$-$C_{10}$-haloalkoxy, $C_1$-$C_{10}$-alkylthio, $C_1$-$C_{10}$-haloalkylthio, $C_1$-$C_{10}$-alkylsulfinyl, $C_1$-$C_{10}$-haloalkylsulfinyl, $C_1$-$C_{10}$-alkylsulfonyl, $C_1$-$C_{10}$-haloalkyl-sulfonyl, $C_1$-$C_{10}$-alkylamino, $C_1$-$C_{10}$-haloalkylamino, di($C_1$-$C_{10}$-alkyl)amino, di($C_1$-$C_{10}$)-haloalkylamino, CN, —$CR^3$=NOH, —$CR^3$=NOCH$_3$ and —$CR^3$=NOC$_2$H$_5$;

$R^2$ is selected from the group consisting of hydrogen, halogen, $C_1$-$C_{10}$-alkyl, $C_1$-.$C_{10}$-haloalkyl, $C_1$-$C_{10}$-alkoxy, $C_1$-$C_6$-alkoxy-$C_1$-$C_6$-alkyl, $C_1$-$C_{10}$-haloalkoxy, $C_1$-$C_{10}$-alkylthio, $C_1$-$C_{10}$-haloalkylthio, $C_1$-$C_{10}$-alkylsulfinyl, $C_1$-$C_{10}$-haloalkylsulfinyl, $C_1$-$C_{10}$-alkylsulfonyl, $C_1$-$C_{10}$-haloalkyl-sulfonyl, $C_1$-$C_{10}$-alkylamino, $C_1$-$C_{10}$-haloalkylamino, di($C_1$-$C_{10}$-alkyl)amino and di($C_1$-$C_{10}$)-haloalkylamino;

$R^3$ is selected from hydrogen, $C_1$-$C_{10}$-alkyl or $C_1$-$C_{10}$-haloalkyl;

A is

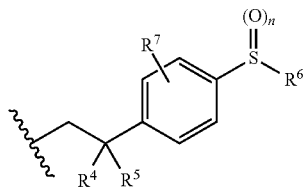 (A.1)

or

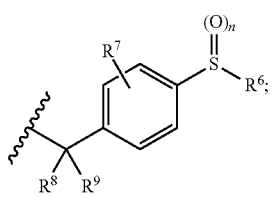 (A.2)

wherein n is 0, 1 or 2;

$R^4$, $R^5$, $R^8$ and $R^9$ are selected independently from one another from hydrogen, CN, $C_1$-$C_{10}$-alkyl or $C_1$-$C_{10}$-haloalkyl;

$R^6$ is selected from the group consisting of trifluoromethyl, —$CH_2$—$CF_3$, —$CF_2$—$CF_3$, $C_2$-$C_{10}$ fluorohaloalkenyl, $C_2$-$C_{10}$ fluorohaloalkynyl and $C_3$-$C_7$ fluorohalocycloalkyl, wherein the carbon atoms of the aforementioned fluorohaloalkyl radicals may further be substituted with $C_1$-$C_{10}$-alkoxy, $C_1$-$C_{10}$-haloalkoxy, cyano and (C=O)$R^q$, and wherein $R^q$ is selected from the group consisting of amino, $C_1$-$C_6$-alkoxy, $C_1$-$C_6$-haloalkoxy, $C_1$-$C_6$-alkylamino, $C_1$-$C_6$-haloalkylamino, di($C_1$-$C_6$-alkyl)amino and di($C_1$-$C_6$)-haloalkylamino;

$R^7$ is selected from the group consisting of hydrogen, halogen, CN, $C_1$-$C_{10}$-alkyl, $C_1$-$C_{10}$-haloalkyl, $C_1$-$C_{10}$-alkoxy, $C_1$-$C_6$-alkoxy-$C_1$-$C_6$-alkyl, $C_1$-$C_{10}$-haloalkoxy, $C_1$-$C_{10}$-alkylthio and $C_1$-$C_{10}$-haloalkylthio;

or an enantiomer, diastereomer or agriculturally or veterinary acceptable salt thereof.

2. A 4-amino-thieno[2,3-d]-pyrimidine compound of formula I according to claim 1, wherein A is

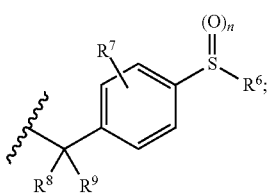 (A.2)

and $R^9$ is selected from the group consisting of hydrogen, $C_1$-$C_{10}$-alkyl or $C_1$-$C_{10}$-haloalkyl.

3. A 4-amino-thieno[2,3-d]-pyrimidine compound of formula I according to claim 1, wherein A is

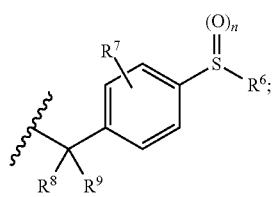 (A.2)

$R^8$ is hydrogen; and $R^9$ is $C_1$-$C_{10}$-alkyl or $C_1$-$C_{10}$-haloalkyl.

4. A 4-amino-thieno[2,3-d]-pyrimidine compound of formula I according to claim 3, wherein A is

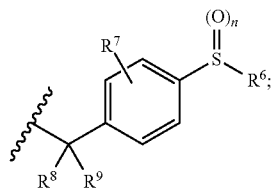 (A.2)

$R^8$ is hydrogen;

$R^9$ is $C_1$-$C_{10}$-alkyl or $C_1$-$C_{10}$-haloalkyl; and wherein the substituents at the chiral carbon atom, where $R^8$ and $R^9$ are bound to, are in (S)-configuration.

5. A 4-amino-thieno[2,3-d]-pyrimidine compound of formula I according to claim 1, wherein A is

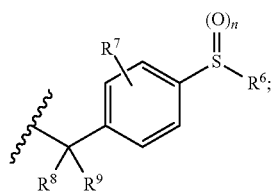 (A.2)

$R^8$ is hydrogen; and $R^9$ is methyl.

6. A 4-amino-thieno[2,3-d]-pyrimidine compound of formula I according to claim 5, wherein A is

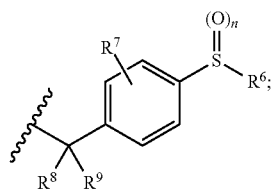 (A.2)

$R^8$ is hydrogen;

$R^9$ is methyl; and wherein the substituents at the chiral carbon atom, where $R^8$ and $R^9$ are bound to, are in (S)-configuration.

7. A 4-amino-thieno[2,3-d]-pyrimidine compound of formula I according to claim 1, wherein
R$^7$ is hydrogen.

8. A 4-amino-thieno[2,3-d]-pyrimidine compound of formula I according to claim 1, wherein
R$^6$ is —CH$_2$—CF$_3$ or —CF$_2$—CF$_3$.

9. A 4-amino-thieno[2,3-d]-pyrimidine compound of formula I according to claim 1, wherein
R$^6$ is trifluoromethyl.

10. A 4-amino-thieno[2,3-d]-pyrimidine compound of formula I according to claim 1, wherein
R$^3$ is hydrogen.

11. A 4-amino-thieno[2,3-d]-pyrimidine compound of formula I according to claim 1, wherein
R$^2$ is selected from the group consisting of hydrogen, halogen, C$_1$-C$_{10}$-alkyl and C$_1$-C$_{10}$ haloalkyl.

12. A 4-amino-thieno[2,3-d]-pyrimidine compound of formula I according to claim 1, wherein
R$^2$ is hydrogen.

13. A 4-amino-thieno[2,3-d]-pyrimidine compound of formula I according to claim 1, wherein
R$^1$ is selected from the group consisting of hydrogen, halogen, C$_1$-C$_{10}$-alkyl and C$_1$-C$_{10}$-haloalkyl.

14. A 4-amino-thieno[2,3-d]-pyrimidine compound of formula I according to claim 1, wherein
R$^1$ is hydrogen or chloro.

15. A 4-amino-thieno[2,3-d]-pyrimidine compound of formula I according to claim 1, wherein
X is halogen.

16. 4-amino-thieno[2,3-d]-pyrimidine compound of formula I according to claim 1, wherein
X is chloro.

17. A 4-amino-thieno[2,3-d]-pyrimidine compound of formula according to claim 1, wherein
n is 0.

18. An agricultural or veterinary composition comprising an effective amount of at least one 4-amino-thieno[2,3-d]-pyrimidine compound of the formula I as defined in any one of claims 1 to 17, and at least one inert liquid and/or solid carrier.

19. Seed comprising an compound of the formula I or an agriculturally useful salt thereof, as defined in any one of claims 1 to 17 in an amount of from 0.1 g to 10 kg per 100 kg of seed.

20. The 4-amino-thieno[2,3-d]-pyrimidine compound for combating or controlling insects, arachnids or nematodes of claim 1, wherein the compound is selected from the group consisting of:

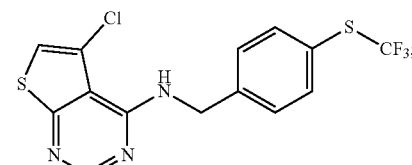

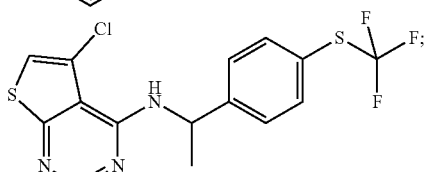

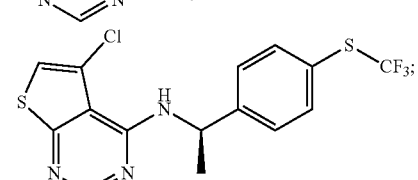

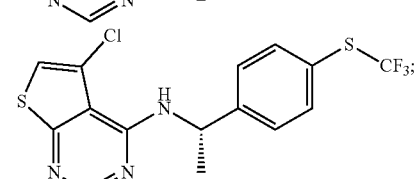

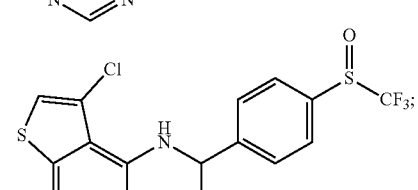

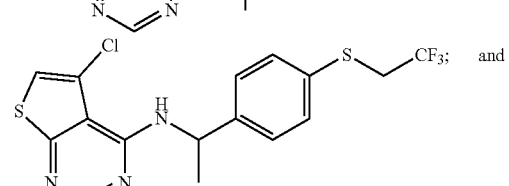

and

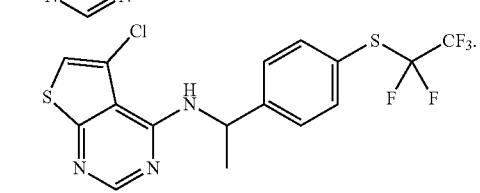

* * * * *